(12) United States Patent
White

(10) Patent No.: US 11,150,081 B2
(45) Date of Patent: *Oct. 19, 2021

(54) THERMAL SENSOR POSITION DETECTING DEVICE

(71) Applicant: Child Mind Institute, Inc., New York, NY (US)

(72) Inventor: Curtis P. White, Brooklyn, NY (US)

(73) Assignee: Child Mind Institute, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/697,176

(22) Filed: Nov. 26, 2019

(65) Prior Publication Data

US 2020/0173769 A1 Jun. 4, 2020

Related U.S. Application Data

(63) Continuation of application No. 16/171,361, filed on Oct. 26, 2018, now Pat. No. 10,520,297, which is a
(Continued)

(51) Int. Cl.

| G01B 11/14 | (2006.01) |
|---|---|
| A61B 5/11 | (2006.01) |
| G01V 8/10 | (2006.01) |
| G06F 3/01 | (2006.01) |
| G01B 11/00 | (2006.01) |
| A61B 5/00 | (2006.01) |
| A61B 5/16 | (2006.01) |
| G01B 11/26 | (2006.01) |

(Continued)

(52) U.S. Cl.
CPC ............ *G01B 11/14* (2013.01); *A61B 5/1114* (2013.01); *A61B 5/16* (2013.01); *A61B 5/6802* (2013.01); *A61B 5/7264* (2013.01); *G01B 11/002* (2013.01); *G01B 11/26* (2013.01); *G01V 8/10* (2013.01); *A61B 5/024* (2013.01); *A61B 5/02405* (2013.01); *A61B 5/14551* (2013.01); *A61B 5/165* (2013.01); *A61B 5/486* (2013.01); *A61B 5/681* (2013.01); *A61B 5/7267* (2013.01); *G06F 3/011* (2013.01)

(58) Field of Classification Search
CPC ....... G01B 11/14; G01B 11/002; G01B 11/26; A61B 5/1114; A61B 5/16; A61B 5/6802; A61B 5/7264; A61B 5/024; A61B 5/02405; A61B 5/14551; A61B 5/165; A61B 5/486; A61B 5/681; A61B 5/7267; G01V 8/10; G06F 3/011
See application file for complete search history.

(56) References Cited

U.S. PATENT DOCUMENTS

| 5,280,265 A | 1/1994 | Kramer |
| 2002/0006807 A1* | 1/2002 | Mantyjarvi ............. G06F 3/011 455/557 |

(Continued)

*Primary Examiner* — David P Porta
*Assistant Examiner* — Jeremy S Valentiner
(74) *Attorney, Agent, or Firm* — Kelley Drye & Warren LLP

(57) ABSTRACT

Devices and methods for determining the position of a device relative to a person using the device, or the position of a part of a user's body relative to the user. One or more thermal sensor may be used to determine the relative position of the device or part of the user's body.

20 Claims, 21 Drawing Sheets

Related U.S. Application Data continuation of application No. 15/816,706, filed on Nov. 17, 2017, now Pat. No. 10,119,807.

(60) Provisional application No. 62/424,131, filed on Nov. 18, 2016.

(51) Int. Cl.
*A61B 5/024* (2006.01)
*A61B 5/1455* (2006.01)

(56) References Cited

U.S. PATENT DOCUMENTS

| | | | |
|---|---|---|---|
| 2007/0075965 A1* | 4/2007 | Huppi | H04W 52/027 |
| | | | 345/156 |
| 2007/0080812 A1 | 4/2007 | Perlman | |
| 2009/0174578 A1 | 7/2009 | Taki | |
| 2011/0144453 A1 | 6/2011 | Kovarik | |
| 2012/0209563 A1* | 8/2012 | Takeda | A63F 13/98 |
| | | | 702/159 |
| 2013/0069985 A1* | 3/2013 | Wong | G02B 27/017 |
| | | | 345/633 |
| 2014/0163333 A1 | 6/2014 | Horseman | |
| 2015/0250419 A1 | 9/2015 | Cooper | |
| 2015/0277557 A1 | 10/2015 | Raffa | |
| 2016/0015280 A1* | 1/2016 | Hyde | A61B 5/1121 |
| | | | 600/301 |
| 2016/0073033 A1* | 3/2016 | Ogasawara | A63F 13/428 |
| | | | 348/207.1 |
| 2016/0255305 A1* | 9/2016 | Ritchey | G06F 3/013 |
| | | | 348/14.03 |
| 2017/0095157 A1* | 4/2017 | Tzvieli | A61B 5/08 |
| 2017/0357397 A1* | 12/2017 | Masumoto | G06F 3/0484 |
| 2018/0173323 A1* | 6/2018 | Harvey | G06T 19/006 |
| 2019/0061159 A1 | 2/2019 | Domae | |

* cited by examiner

THERMAL SENSOR POSITION DETECTING DEVICE

CROSS-REFERENCE TO RELATED APPLICATIONS

This application is a continuation of U.S. patent application Ser. No. 16/171,361, filed on Oct. 26, 2018, which is a continuation of U.S. patent application Ser. No. 15/816,706, filed Nov. 17, 2017, which claims the benefit of U.S. Provisional Patent Application No. 62/424,131, filed Nov. 18, 2016. The entire contents of those application are incorporated herein by reference.

FIELD OF THE INVENTION

This invention relates to the field of position detection and, more particularly, to the use of one or more sensors to determine the position of the sensors or a device containing the sensors relative to a person's body.

BACKGROUND OF THE INVENTION

In various fields and applications, accurately determining the position of an object relative to a person holding or wearing the object, or the position of part of a person's body (e.g., a person's hand) relative to another part of the person (e.g., the person's head) is critical to successfully achieving a desired outcome. For example, virtual reality applications being developed today seek to render parts of a user's body, e.g., their arms and hands, within the digital world rendered by the application. The virtual reality application may show the person's arms and hands moving within the rendered digital world and interacting with virtual objects. Accurately determining the location and movement of the user's arms and hands would allow the virtual reality application to present a realistic experience to the user.

Accurately determining the position of part of a person's body relative to the person is also useful in the treatment of unconscious and unwanted behaviors, including the treatment of trichotillomania (hair-pulling disorder) excoriation (skin-picking disorder), nail biting and thumb sucking. Those who engage in these behaviors are often not aware that they are engaging in them. Studies have shown that if people are alerted when they are unconsciously engaging or about to engage in unwanted behaviors of this sort then they are less likely to engage in the unwanted behavior. Studies have shown that devices that provide this service can lead to long term, continual and independent cessation of the behavior.

Trichotillomania, also called hair-pulling disorder, is a mental disorder that involves recurrent, irresistible urges to pull out hair from the scalp, eyebrows or other areas of the body, despite efforts to stop. Hair pulling from the scalp often leaves patchy bald spots, which cause significant distress and can interfere with social or work functioning. People with trichotillomania may go to great lengths to disguise the loss of hair. For some affected people, trichotillomania may be mild and generally manageable. For others, the compulsive urge to pull hair is overwhelming or unconscious.

Excoriation disorder, also known as skin-picking disorder, involves repetitive and compulsive picking of skin which results in tissue damage. Episodes of skin picking are often preceded or accompanied by tension, anxiety, or stress. The region most commonly picked is the face. Most patients with excoriation disorder report having a primary area of the body that they focus their picking on. Complications arising from excoriation disorder include: infection at the site of picking, tissue damage, and septicemia. Damage from picking can be so severe as to require skin grafting.

Hair pulling, skin picking, nail biting, thumb sucking and similar unwanted manipulation of the body can all take place unconsciously. Studies have shown that making individuals more aware that they are participating in these behaviors greatly decreases their propensity to engage in these behaviors in the future. CBT (Cognitive Behavioral Therapy) and ACT (Acceptance and Commitment Therapy) are both used to treat harmful hair-pulling and skin-picking behavior, but are not always effective. The present inventive device can be used in conjunction with talk therapies to increase the effectiveness of treatment. Talk therapies tend to focus on conscious thought processes. The present inventive device provides a therapeutic intervention during or before unconscious pulling of the hair or picking of the skin, a situation in which introspection and reflective decision making encouraged by CBT cannot apply.

Thumb sucking is normal in babies and young children. In some cases, thumb sucking after age 5 is done in response to an emotional problem or other disorder, such as anxiety. Children who suck their thumbs often or with great intensity around age four or five, or those who are still sucking their thumbs at age 6 or later, are at risk for dental or speech problems. Prolonged thumb sucking may cause the teeth to become improperly aligned (malocclusion) or push the teeth outward. Unhealthy thumb sucking has been treated with a blocking device worn on the hand which physically impedes thumb sucking, as well as the application of a bad tasting substance applied to the thumb to dissuade thumb sucking. Both of these treatments may be uncomfortable or even painful to a child. Both of these treatments may also be outside the bounds of culturally acceptable child care.

There are devices in existence (such as HabitAware Liv™) which are worn around the wrist, use an accelerometer or other relative position sensor, detect gestures correlated to unwanted behaviors and provide vibrotactile feedback to the user, making them aware of the gesture. These devices may consist of the following components: a relative position sensor (accelerometer, gyroscope, magnetometer, etc.), a processing unit (microcontroller or System on Chip such as ARM Cortex family), and a radio transceiver such as a Bluetooth and a vibration motor. Examples of this combination and configuration of hardware components are activity trackers such as the FitBit™. The HabitAware Liv™ device essentially consists of the same mechanical and electrical parts as a commonly available activity tracker, such as the FitBit™, configured to detect a gesture of the hand (such as raising of the hand to unconsciously pull hair) instead of the steps taken during running or walking and other common activities. Similar configurations of sensors, processing units and feedback mechanisms exist to monitor sleep; in fact, the same device can sometimes be used to monitor walking and sleep. In many cases the device "syncs" or connects to a software program on a computer or smartphone, often connected to an internet platform or online "cloud" platform.

Prior devices that rely on accelerometers and other relative position sensors cannot "dead reckon" their position relative to another object. For example, the sensors may detect the angular position of the device relative to gravity, but they cannot detect whether the device is above, below or to the side of the user's head or any other object. There is therefore a need for improvements in devices that overcome some or all of the previously described drawbacks of prior options. The present inventive device differs from the HabitAware Liv™ and other prior devices by providing novel and inventive means to decrease false positive feedback, i.e., feedback that is mistakenly provided by the prior device when the target gesture is not taking place. The present inventive device further increases the likelihood of detecting unwanted behavior events which warrant feedback.

SUMMARY OF THE INVENTION

The present invention is directed to improved devices that may be used to determine the position of each device relative to a person using the device, or the position of a part of a user's body relative to the user. The present invention is further directed to improved methods for using such devices. Specifically, the present invention uses at least one thermal sensor which, in combination with a data-processing unit, can be used to determine the position of the device or part of the user's body relative to the user.

In one embodiment of the present device, a thermal sensor such as a contactless thermometer allows the device to sense whether it is pointed at the user's body (the body having a higher temperature than surrounding areas or other objects), which enables the device's data processing algorithm to combine the relative position of the accelerometer with the absolute position of the device in relation to the user's body. This technique at least partially overcomes the "dead reckoning" challenges associated with using only accelerometers, gyroscopes and/or magnetometers.

Adding additional thermal sensors may allow the device to create a more detailed heat map for a more nuanced determination of the position of the device relative to the person's body. Orienting the thermal sensors so they are facing in different directions relative to each other may increase the field of vision of the thermal sensors and further improve the position assessment.

Additional embodiments of the present inventive device may include sensors to detect physiological characteristics such as increased heart rate that may be associated with one or more emotive states, such as stress. The emotive states may be indicative of undesirable behavior, which the device may be designed to detect, or may serve to minimize false positive feedback/or and missed events, which warrant feedback in a fashion superior to prior devices.

Numerous variations may be practiced in the preferred embodiment.

BRIEF DESCRIPTION OF THE DRAWINGS

A further understanding of the invention can be obtained by reference to embodiments set forth in the illustrations of the accompanying drawings. Although the illustrated embodiments are merely exemplary of systems, methods, and apparatuses for carrying out the invention, both the organization and method of operation of the invention, in general, together with further objectives and advantages thereof, may be more easily understood by reference to the drawings and the following descriptions. The drawings are not intended to limit the scope of this invention, which is set forth with particularity in the claims as appended hereto or as subsequently amended, but merely to clarify and exemplify the invention.

DETAILED DESCRIPTION OF THE INVENTION

The invention may be understood more readily by reference to the following detailed descriptions of preferred embodiments of the invention. However, techniques, systems, and operating structures in accordance with the invention may be embodied in a wide variety of forms and modes, some of which may be quite different from those in the disclosed embodiments. Consequently, the specific structural and functional details disclosed herein are merely representative, yet, in that regard, they are deemed to afford the best embodiment for purposes of disclosure and to provide a basis for the claims herein, which define the scope of the invention. It must be noted that, as used in the specification and the appended claims, the singular forms "a", "an", and "the" include plural referents unless the context clearly indicates otherwise.

Figure 1:
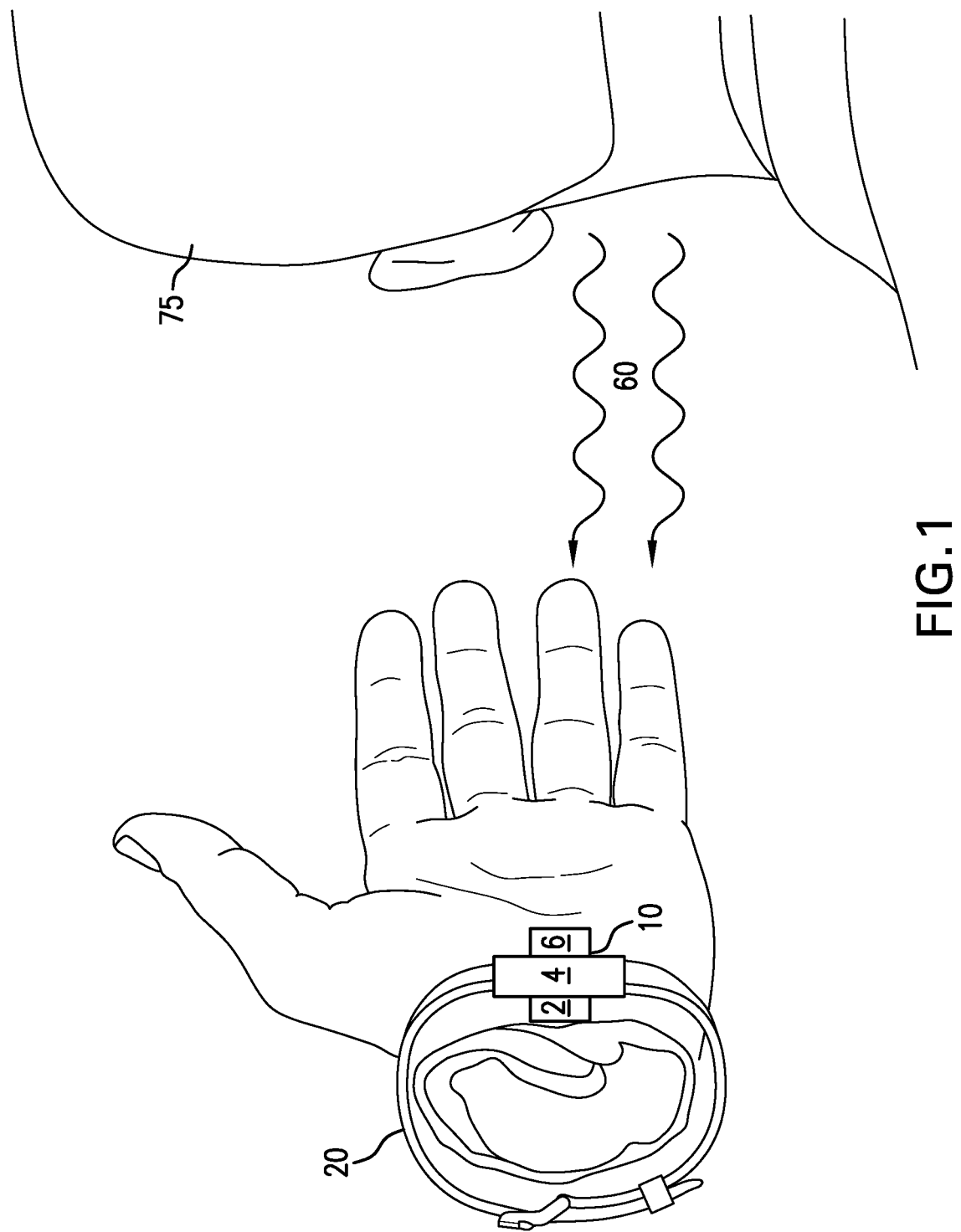
FIG. 1 depicts a first embodiment of the present inventive device, mounted on a cross section of a user's wrist.

Referring to FIG. 1, there is shown sensor device (10), an embodiment in accordance with the present invention. Sensor device (10) is shown worn on the underside of a user's wrist. Sensor device (10) may be held against the user's wrist by strap (20). A portion of the user's head (75) and an indication of thermal radiation (60) emanating from the head (75) are also illustrated.

Sensor device (10) may include sensors contained in or mounted on a unit (enclosure, attachment, or similar container or base) held close to or against the wrist by means such as a strap or similar fastening. For illustrative purposes only, sensor device (10) is shown in FIG. 1 divided into three parts: portions (2), (4), and (6). Portion (2) may include a sensor or sensors facing and in contact with the user's wrist, portion (4) may include all components of sensor device (10) which are not external sensors, and portion (6) may include a contactless sensor or sensors to detect the presence and/or distance of sensor device (10) from the head (75), mouth or other significant body area. The portions (2), (4), and/or (6) or one or more components included in portions (2), (4), and/or (6) may be contained in a single enclosure or may be contained in more than one enclosure.

The sensors in portion (2) may include a pulse oximetry heart rate and heart rate variability sensor. This sensor may determine the user's blood oxygen levels, which is indicative of heart behavior, by detecting the body's absorption of red and infrared light. One example of such a sensor is the Maxim Integrated MAX30100™.

In one embodiment, portion (2) may also be absent from sensor device (10). In this embodiment, there may be no sensor in contact with the wrist. The only sensors included in sensor device (10) may be a relative position sensor and a contactless thermometer which may be included in portion (6).

Portion (4) may include one or more sensors, such as an accelerometer, gyroscope, and/or magnetometer. These sensors may serve to determine the angular position of sensor device (10) relative to gravity and/or the acceleration of sensor device (10) in a given direction. Portion (4) may also include components such as a battery, a battery charge/discharge regulator, a data processing unit such as a microcontroller of a SoC (System on Chip) computer, a vibration motor, a vibration motor power driver, a wired data interface such as a USB port, and/or a wireless data radio such as Bluetooth or WIFI. One or more of these components may be mounted on a printed circuit board (PCP), and the PCP may be enclosed within an Acrylonitrile Butadiene Styrene (ABS) plastic enclosure. This enclosure may contain ports for outside facing sensors such as the MAX30100™ and the Melexis MLX90614™.

Portion (6) of sensor device (10) may include a contactless sensor located on the underside of the wrist and pointed away from the wrist. The contactless sensor may determine the distance, presence, or characteristics (such as pulse or respiration) of the user's body. This sensor may be an active sensor, for example a proximity sensor which emits infrared radiation from a light emitting diode (LED) and detects, using an infrared phototransistor, the infrared radiation after it reflects off the user's body and/or another object. The sensor may emit a predetermined wavelength between 100 nanometers and 1000 nanometers. For example, portion (6) may include the Vishay VCNL4010™ active infrared position sensor and/or the Avago APDS-9960™ active infrared integrated gesture detection sensor. In the alternative, the contactless sensor may be a passive sensor, such as a pyrometer (i.e., contactless thermal sensor) which passively receives the infrared energy radiated by the body or other source, converts that radiation into electricity, amplifies the electricity and uses the resulting signal to determine the temperature of the surface at which it is pointed. Examples of thermopile-based contactless thermometers that may be employed include the Melexis MLX90614™ and the Texas Instruments TMPOO7™. Thermal radiation (60) emitted from a user's head (75) is shown in FIG. 1. In addition, or in the alternative, portion (6) may include an ultrasonic transducer, a LIDAR module such as the STMicroelectronics VL6180X, or a component for measuring the volume of reflected light.

By incorporating a contactless thermal sensor such as a pyrometer into the sensor device (10) and facing away from the wrist, sensor device (10) may, for example, detect that the wrist is pointed towards an area that is not the user's body, such as a bookcase at room temperature (e.g., 70 degrees Fahrenheit), instead of the user's body, which might be detected as 90 degrees Fahrenheit, assuming minor obstruction by hair.

Similarly, if a child were wearing sensor device (10) to provide feedback when the child attempts to suck the child's thumb, using a position/motion sensor alone might cause sensor device (10) to provide false positive feedback when the child reaches up to clutch his/her chest. Incorporating a thermal sensor in sensor device (10), such as a pyrometer, may allow sensor device (10) to differentiate among different parts of the body, not merely the presence of the body in contrast to other objects. For example, the temperature detected by the pyrometer when the child is actually sucking his/her thumb might be 95 degrees Fahrenheit, while the temperature detected when the child is clutching his/her chest might be 85 degrees because of the obstruction of clothing between the device and the body.

When the user makes an undesirable gesture related to an unwanted behavior, the angular position and/or movement of the hand may be consistent and predictable. In the case of addressing a user who engages in hair pulling, for example, if the user reaches to pull his/her hair, the user's wrist will necessarily be pointed in the direction of the body. By matching the angular position and/or movement of a sensor device in accordance with the present invention with the predictable angular position and/or movement of the hand during an undesirable gesture, the sensor device may detect the undesirable gesture and may provide immediate feedback or relevant data to the user.

Detecting that the wrist is pointed at the body by measuring the temperature of the body surface immediately opposite the inventive device indicates that the behavior gesture to be detected (reaching for the hair) is occurring. If position is detected using only a relative position sensor such as an accelerometer, gyroscope, magnetometer or combination thereof, and no contactless thermometer is used, false positive matches may occur because the angular position or movement signature used to detect the undesirable gesture may match other gestures. For example, a false positive gesture detection might occur if the user reaches at least to the height of their head to collect a book from a book shelf. In that situation with the present invention, however, the device's contactless thermometer on the bottom of the wrist would be at least partially pointed towards the bookcase and indicate the ambient temperature, or at least a lower temperature than if the contactless thermometer were pointer toward the user. Thus, the contactless thermometer could allow the device to screen out this false positive gesture detection.

Referring again to sensor device (10) shown in FIG. 1, portion (2) may include a sensor or sensors near or immediately adjacent to the user's skin, such as the underside of the user's wrist. Such sensor or sensors may detect physiological characteristics of the user which may be associated with the unwanted behavior. For example, the user may engage in unwanted behavior because the user is under stress. The physiological characteristics of psychological stress such as a faster pulse may be detected by sensor device (10) and contribute to determining when a gesture related to a negative habit is likely to take place. In addition to detecting when a gesture related to a negative habit is likely to take place outright, the detection of physiological characteristics and various bioindicators may be used in combination with other sensors such as accelerometers and contactless thermometers to help reduce false positives that might otherwise be generated if those sensors were used by themselves.

Until recently, physiological characteristics such as pulse and respiration could only be determined by sensors in contact with a person's skin. There are now contactless sensors which may be able to detect a person's respiration and pulse from a distance. Accordingly, the use of biosensing device sensors in contact with the user's skin may be replaced by corresponding contactless sensors mounted on a sensor device and pointed towards the user's body.

A sensor device in accordance with the present invention may include a means for providing feedback to the user. For example, the sensor device may include a component for providing physical or haptic feedback to the user. A vibrating motor may be included in the sensor device to provide a physical stimulus. In addition, or in the alternative, a sound emitting unit may be included in the device to provide an auditory signal. In addition, or in the alternative, one or more lights or display screens or other similar components may be used to provide a visual response or status indication to the user.

The device may also include one or more processors. The processors may control the sensors and/or the means for providing feedback. The processors also may be used to collect data from the sensors. The processors may also transfer data, including data from the sensors, between the processors and memory on the device or to a separate device. For example, data collected by one or more sensors in the device may be transferred to a separate device such as a desktop computer, laptop computer, router, computer tablet, mobile phone, or smart watch operated by the user. The transfer may be made by a cable using a communication protocol such as USB (Universal Serial Bus), serial post communication, or a Local Area Network. Alternatively, the transfer may be made wirelessly using a wireless protocol such as Bluetooth, WiFi, or infrared Pulse Width Modulation (PWM). An application or custom software on the inventive device or on a separate device may record and make use of data gained from the device's sensors and device sensor data processing. The data may also be transferred to an internet cloud storage application.

Figure 2:
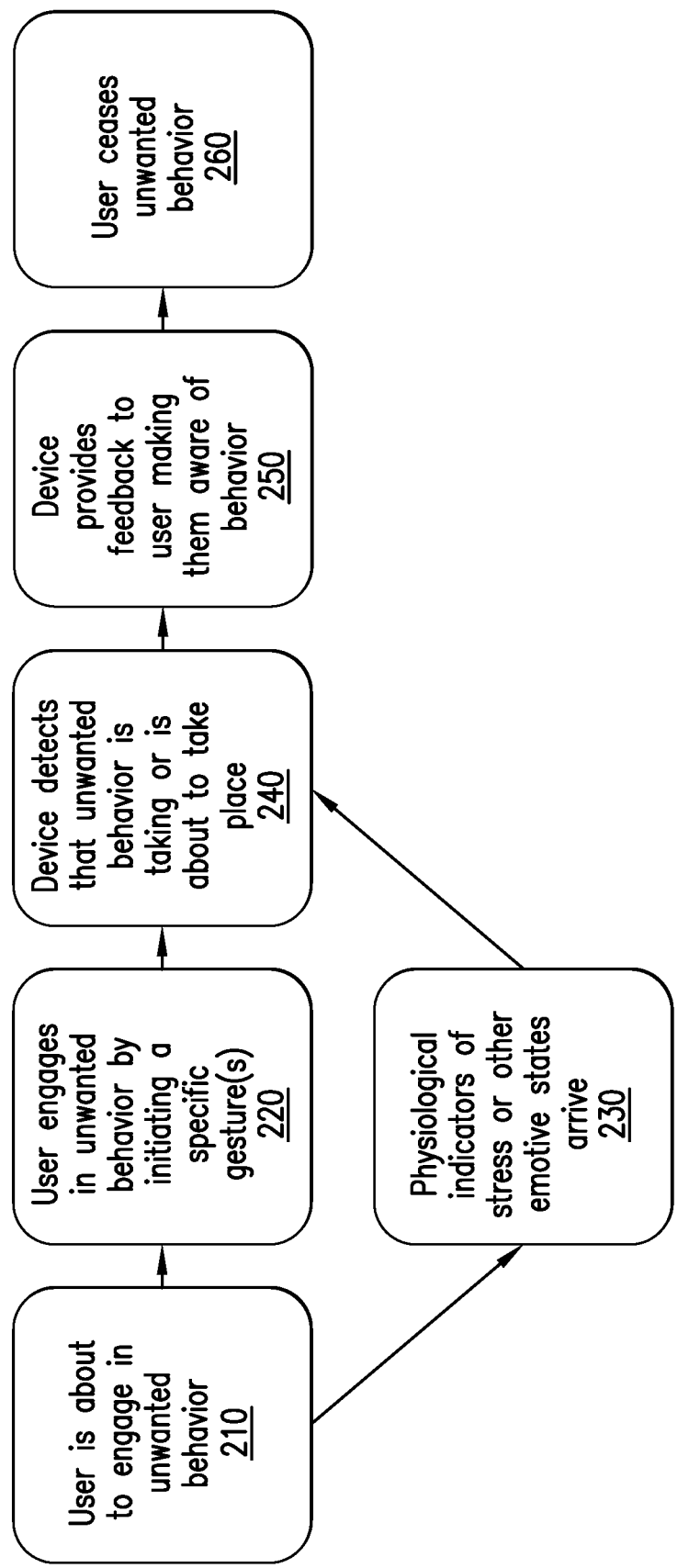
FIG. 2 depicts an exemplary sequence of events over time in which the device depicted in FIG. 1 is used to detect and indicate an undesirable behavior.

Referring to FIG. 2, depicted is a method for treating an unwanted behavior using the present invention. Step (210) describes the time just before the user engages or attempts to engage in the unwanted behavior. At this time the user may have physiological indications of stress or anxiety which precede the unwanted behavior. At Step (220), the user has just begun or is in the midst of executing the gesture related to an unwanted behavior, such as moving the hand towards the hair to pull it. The angular position of the device as measured on three axes (x, y, z) by a relative position sensor or combination of sensors such as accelerometer, gyroscope, or magnetometer will shift in a predictable and detectable fashion when this gesture is partially or fully executed.

Step (230) is the period at which the emotive state of the user may change from the user's baseline to an anxious or aroused state which predictively precedes the unwanted behavior. At this point, physiological indicators such as heart rate which are correlated to the shift in emotive state will also change in a predictable and detectable fashion. This may occur before or in the midst of the unwanted behavior.

Step (240) is the period at which the device detects that the user is engaging or about to engage in the unwanted behavior by: (1) detecting that the user's physical movement and/or position of the device matches a predictable movement and/or position associated with a gesture related to the unwanted behavior, for example the user's hand reaching to pull his/her hair; (2) the presence and position of the user's body opposite the device as determined by a contactless sensor such as an infrared thermopile contactless thermometer; and (3) in one but not all embodiments, the emotive state of the user as determined by one or more physiological indicators such as heart rate as indicated by, for example, a pulse oximetry heart rate sensor. The device may match the x,y,z angular position of the device to the predicted x,y,z angular position associated with the gesture. In the alternative, the device may analyze the x,y,z angular position of the device over a period of time and over multiple sensor readings. Multiple sensor readings and their relationship over time may be compared to information corresponding to the angular position associated with the gesture to be detected to determine whether the gesture is occurring.

Once the device has combined data from multiple sensors to provide a reliable and dependable indication that feedback should be provided, at Step (250) of FIG. 2, the inventive device may provide feedback to the user. Power may be supplied to a small vibration motor, causing vibrations to be transmitted from the motor to the surface of the user's skin. The vibrations may be strong enough to alert the user that the device has been activated. The feedback may also be so severe that it causes physical discomfort which inhibits the unwanted behavior even if the user consciously tries to engage in the behavior.

In one embodiment, the vibrations may continue until the user turns the vibrations off by, for example, using a switch on the device or a setting on a smart phone paired with the device. In another embodiment the vibration motor may turn off when the sensors indicate that the user is no longer engaged or about to engage in a gesture associated with the unwanted behavior.

At Step (260) of FIG. 2, after the device has provided feedback and the user has been made aware that the user is about to engage in an unwanted behavior, the user has chosen not to engage in the undesirable behavior. Over time, this process may result in the cessation of the unwanted behavior even when the device is not being worn.

Figure 3:
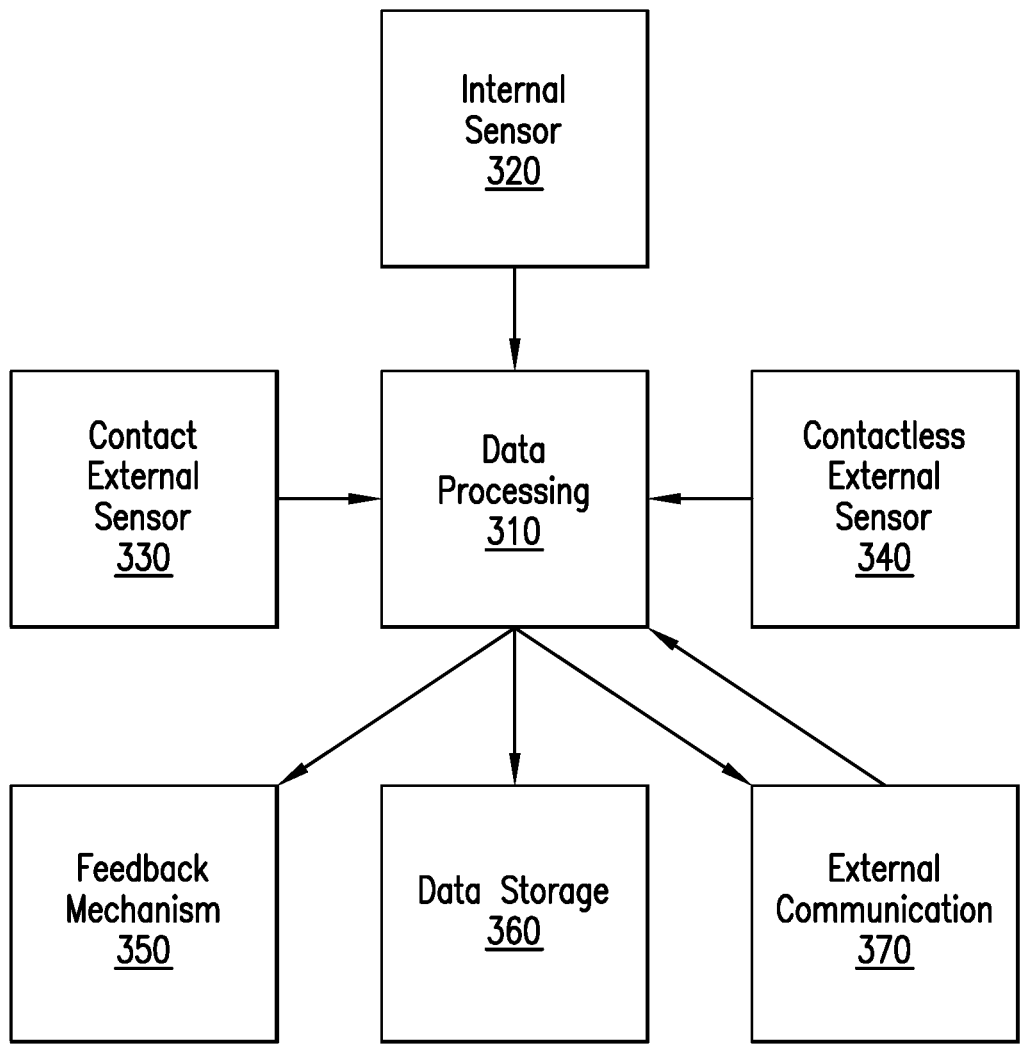
FIG. 3 depicts a conceptual outline of the discrete components which may make up the first embodiment of the present inventive device.

FIG. 3 depicts a conceptual outline of exemplary inventive sensor device components and their relation to each other. One embodiment of the sensor device may include data processing unit (310) (e.g., ARM Cortex™ M0 SoC (System on Chip) microcontroller embedded in a Nordic nRF51822™ integrated 2.4 GHz Bluetooth transceiver); internal sensor (320) (e.g., InvenSense MPU6O5O™ accelerometer); contact external sensor (330) (e.g., Maxim Integrated MAX30100™ pulse oximetry sensor); contactless external sensor (340) (e.g., Texas Instruments TMPOO7™ infrared thermopile contactless thermometer); feedback mechanism (350) (e.g., 3.3 v coin vibration motor drawing 50 mAh, diameter 10 mm height 2 mm); data storage (360) (e.g., Micro SD Card and interface circuit); and/or external communication module (370) (e.g., Nordic nRF51822™ integrated 2.4 GHz Bluetooth transceiver and micro USB plug).

Internal sensor (320), contact external sensor (330), and contactless external sensor (340) may interface with data processing unit (310) using a two wire i2c bus. Feedback mechanism (350) may be powered by a MOSFET transistor driver controlled by a digital i/o signal from data processing unit (310) ARM MO microcontroller. All the aforementioned components may be powered by a 15 OrnAh 3.7 v lithium polymer rechargeable battery. Battery overcharge/undercharge components (not shown) may also be present in the sensor device. The sensor device battery may be recharged from the micro USB port power leads by way of, for example, a MAX1555 lithium polymer battery management integrated chip. Another exemplary embodiment may include all the elements listed above with the exception of contact external sensor (330).

Figure 4B:
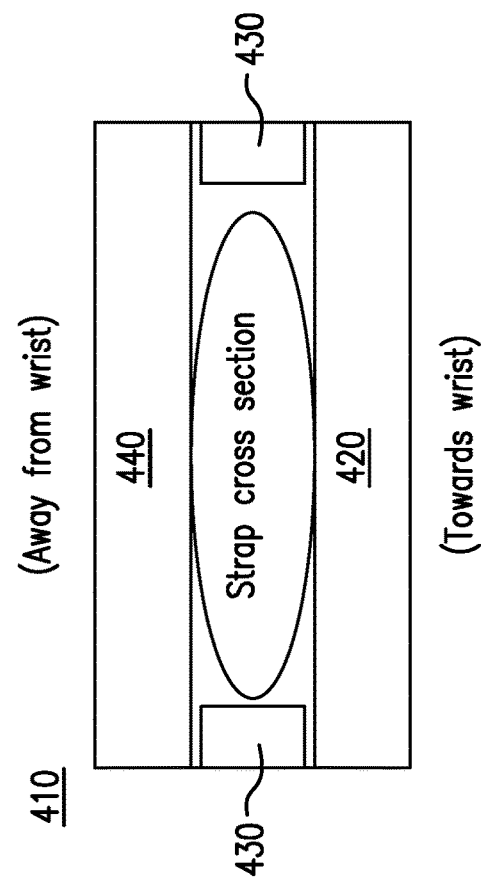
FIGS. 4A and 4B depict a specific embodiment of the inventive device wherein the device is contained in a loop which may be mounted around the underside of a watchstrap, bracelet, or other strap worn around the wrist.
Figure 4A:
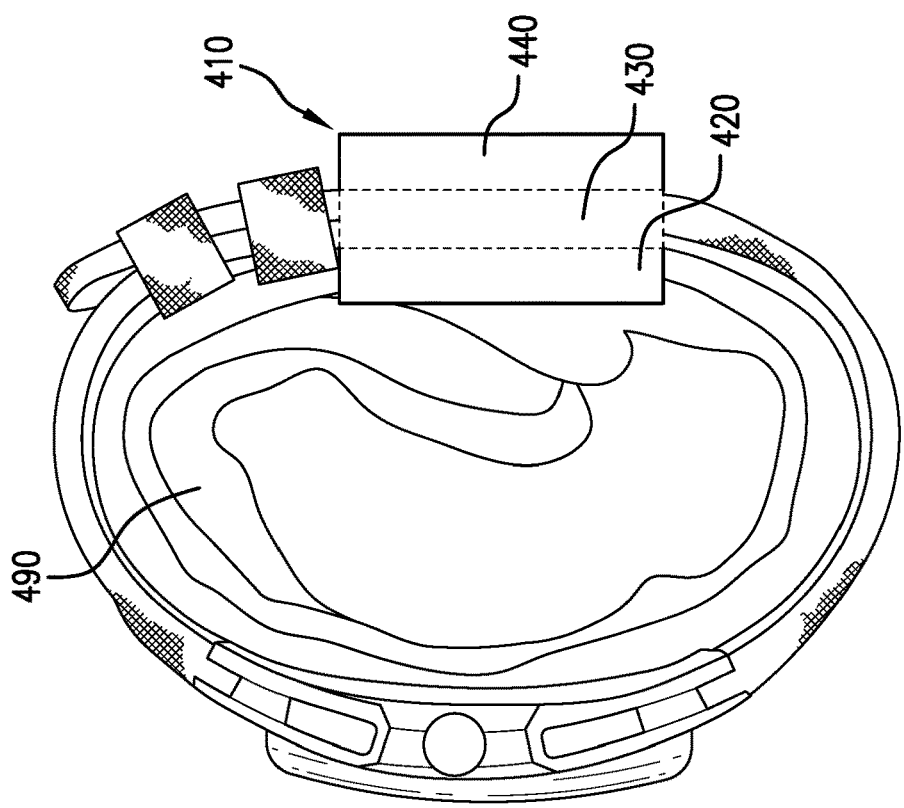

FIGS. 4A and 4B depict an embodiment of sensor device (410) mounted in a loop worn around a watchband, bracelet or other strap worn around the wrist. FIG. 4A depicts a side profile cross section of sensor device (410) and a user's wrist (490), and FIG. 4B depicts a top close-up cross section of sensor device (410).

Some people, especially those suffering from anxiety, which often coincides with compulsive behaviors, may be too self-conscious about the appearance of a device such as the Fitbit™ or HabitAware Liv™ to consider their use. By hiding sensor device (410) under the wrist, in an inconspicuous loop around the wristband of a secondary, more aesthetically pleasing and socially acceptable device such as a watch, the anxiety may be reduced. In one such embodiment the loop is at least partially or wholly made from silicone rubber and stretches around the target strap it surrounds.

Sensor device (410) components may be separated into two halves, some between the wrist and the strap, and the rest above the strap, and the two halves may be joined together by sections (430). Section (420) represents the portion of the loop between the strap, such as a watchband, and the wrist. A component for providing vibrotactile feedback such as a vibration motor (e.g., feedback mechanism (350) of FIG. 3) may be located in section (420), where vibrations are best felt by the user. A contact sensor, such as a Maxim Integrated MAX30100™ pulse oximetry sensor, may be located here as well.

Section (440) represents the portion of the loop at least partially covering the surface of the strap and facing away from the user. A contactless sensor, such as the Texas Instruments TMPOO7™ infrared thermopile contactless thermometer, may be located in section (440) where it may receive infrared radiation from objects opposite the device. A relative position sensor such as the InvenSense MPU6O5O™ accelerometer, a battery, a microcontroller, data storage, a wireless communication transceiver, and a battery charger may be located in section (420) in one embodiment, in section (440) in another embodiment and all possible individual component distribution combinations between those elements in additional embodiments.

Sensor device (410) may include one thermal sensor or an array of thermal sensors to detect the presence or absence of a human body (e.g., head, torso), and to determine the position of the sensors relative to the body if a body is detected. When more than one thermal sensor is used, preferably the thermal sensor elements are spaced apart and/or oriented so they are not pointing in the same direction. For example, each thermal sensor may be positioned at least one centimeter apart from any other thermal sensor included in the device. As another example, a first thermal sensor may be directed in a first direction, and a second sensor may be directed in a second direction, wherein the second direction is not parallel to the first direction. By using multiple independent thermal sensors spread across the surface of the device, more valuable data may be obtained at close range.

Figure 5:
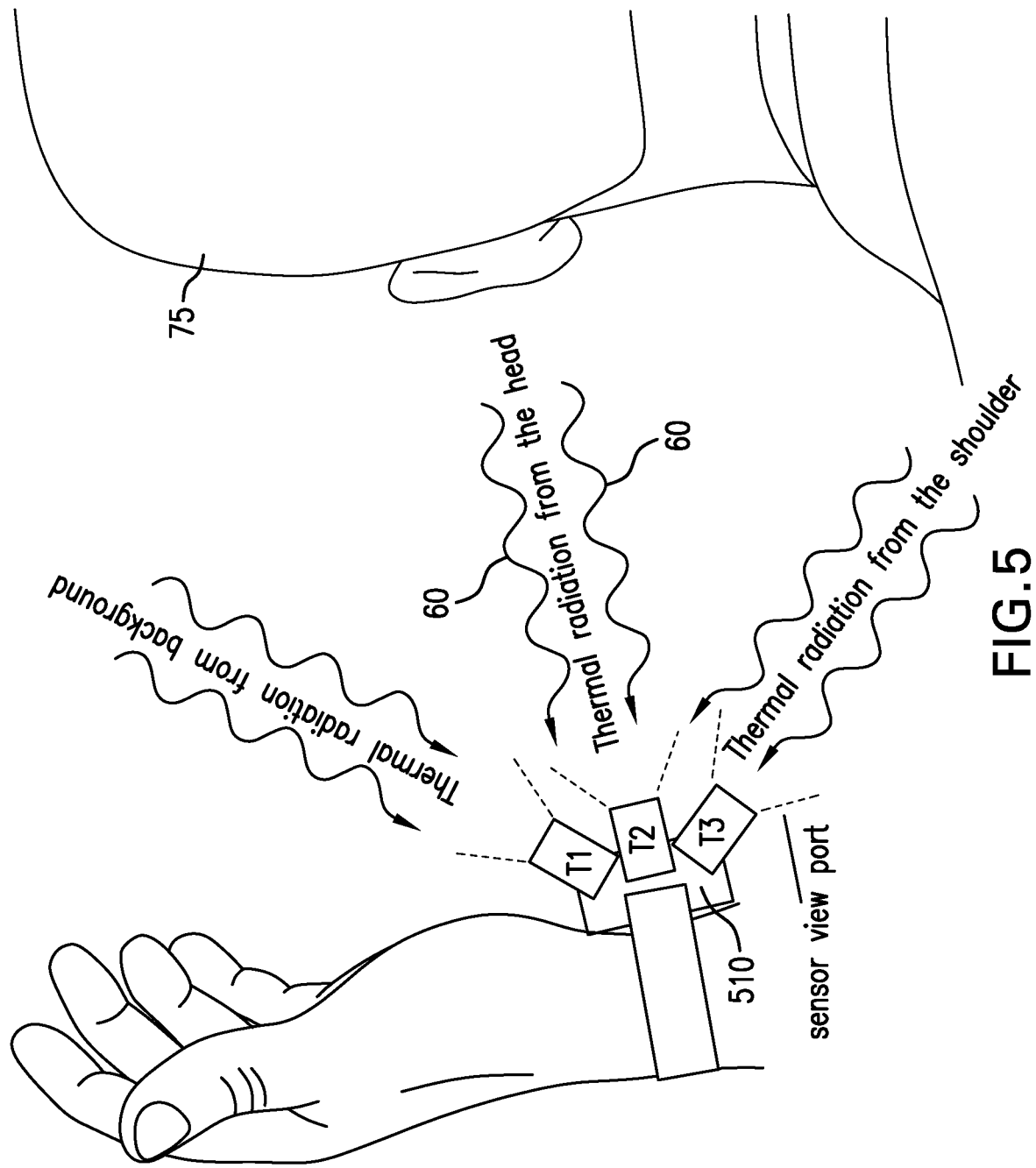
FIG. 5 depicts an exemplary profile of thermopile sensor coverage.
Figure 6:
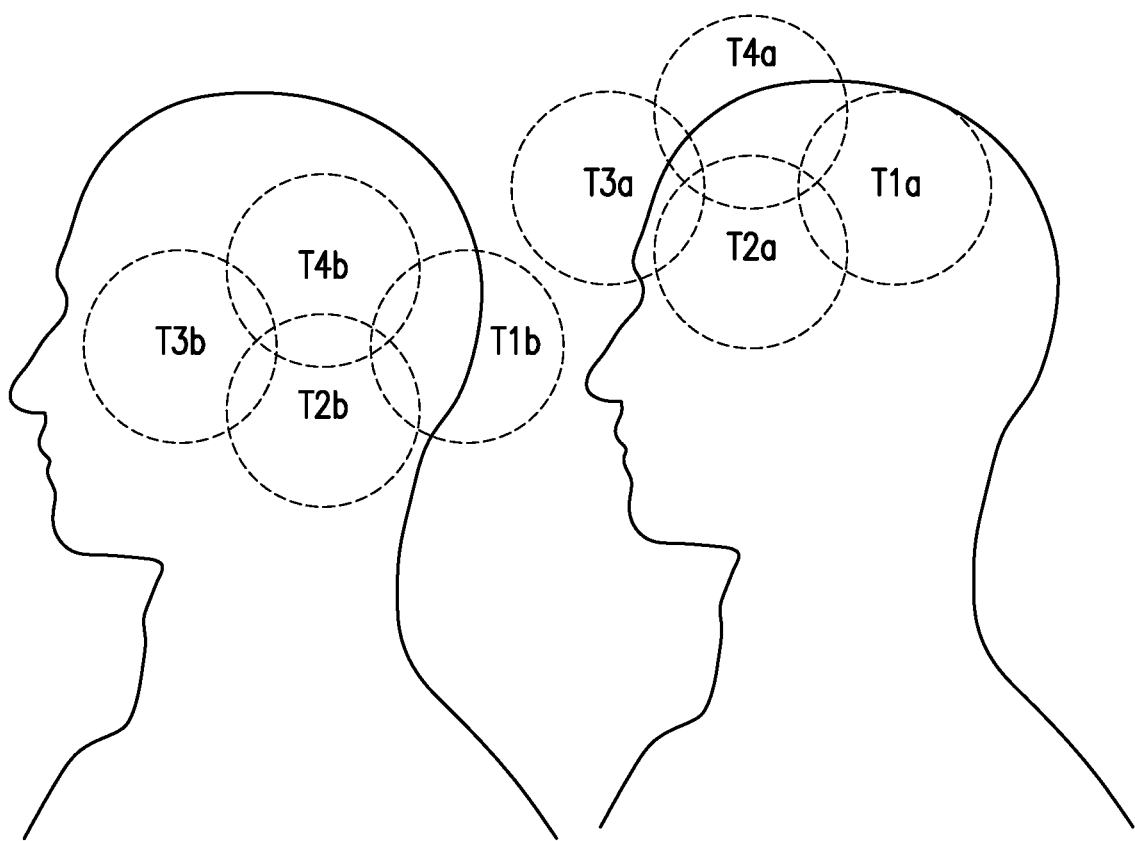
FIG. 6 depicts exemplary thermopile sensor coverage areas.
Figure 7A:
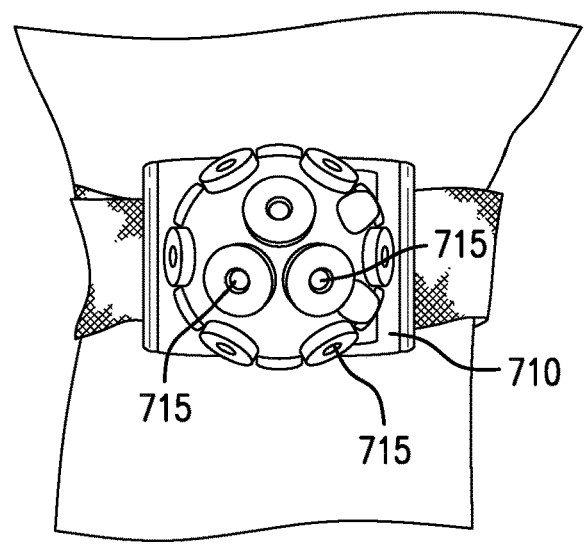
FIGS. 7A-7C depict orthogonal views of an exemplary embodiment of the present inventive device.
Figure 7B:
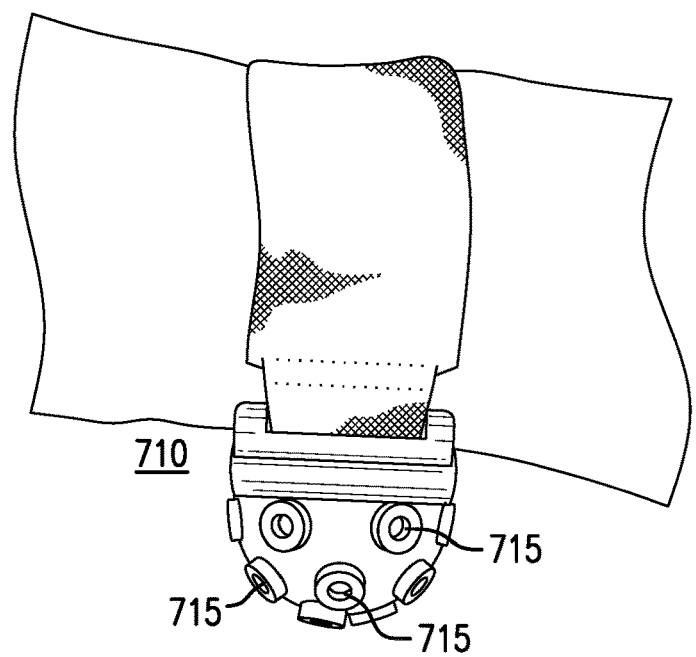
Figure 7C:
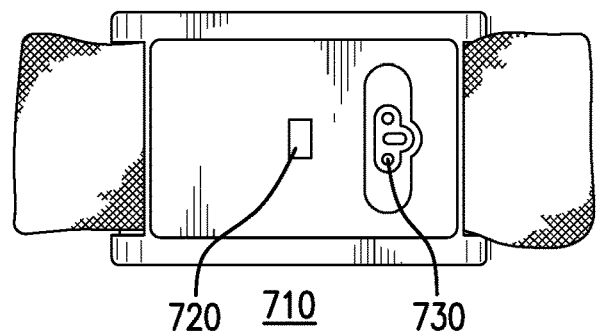

FIGS. 5 and 6 illustrate differentiation of thermopile sensor values as determined by viewport coverage around the head. In FIG. 5, sensor device (510) is depicted with three thermopiles (T1, T2, T3) for ease of illustration, though the number of thermopiles may be higher or lower than three. Thermopiles (T1, T2, T3) are oriented to face in different directions to provide a wider field of view than if they were aligned in parallel. As shown in FIG. 5, radiation emitted or reflected from the user's shoulder, the user's head (75), and the area above the user's head may be detected simultaneously by sensor device (510). Sensor device (510) might also contain additional components as described above, including, for example, a heart rate sensor or temperature sensor facing the skin.

FIG. 6 illustrates a sample comparison between thermopile array coverage patterns. The thermopile sensor value is an average across the area of reception. As an illustrative example, if the body is assumed to uniformly emit thermal radiation corresponding to a surface temperature of 100 degrees, and the background corresponds to a temperature of zero degrees, areas T2$a$, T4$b$, T2$b$ and T3$b$ would read a value of 100, while areas T4$a$ and T1$b$ would read approximately 60. As a thermopile pans from an object of temperature x across a boundary to an object of temperature y, it will produce a gradient from x to y. This occurrence may be used for edge detection.

The shape of thermopile coverage areas is simplified in FIG. 6. Circular-shaped coverage implies that the thermopile direction is perpendicular to the target surface (head). However, if the thermopiles are positioned so that no thermopile is parallel to any other thermopile, no more than one thermopile may be perpendicular to any given surface at one time. When a thermopile is not oriented so as to be perpendicular to a target surface, the coverage area would be a non-circular ellipse.

Coverage areas T1$a$ and T3$a$ (or alternatively T1$b$ and T3$b$) may correspond to thermopiles positioned furthest away from the center of the wrist or sensor device, and may, for example, point approximately 160 degrees from each other. In that example, as the device changes proximity from the head, thermopile array coverage area ("viewport" or "viewing" area) will change greatly, providing an advantage over a flat integrated grid thermopile array sensor or thermal cameras, which include sensors that all point in the same direction.

Figure 8:
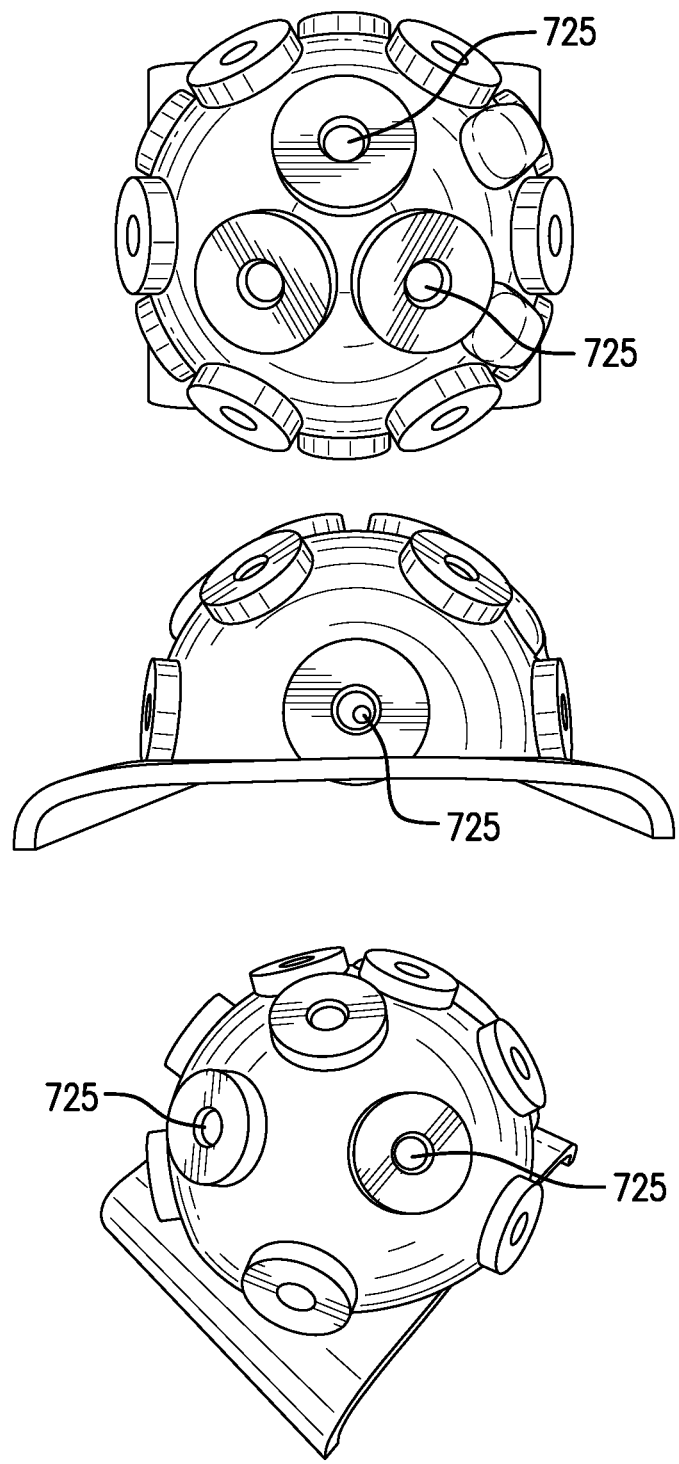
FIG. 8 depicts orthogonal views of an enclosure for the device depicted in FIGS. 7A-7C.
Figure 9:
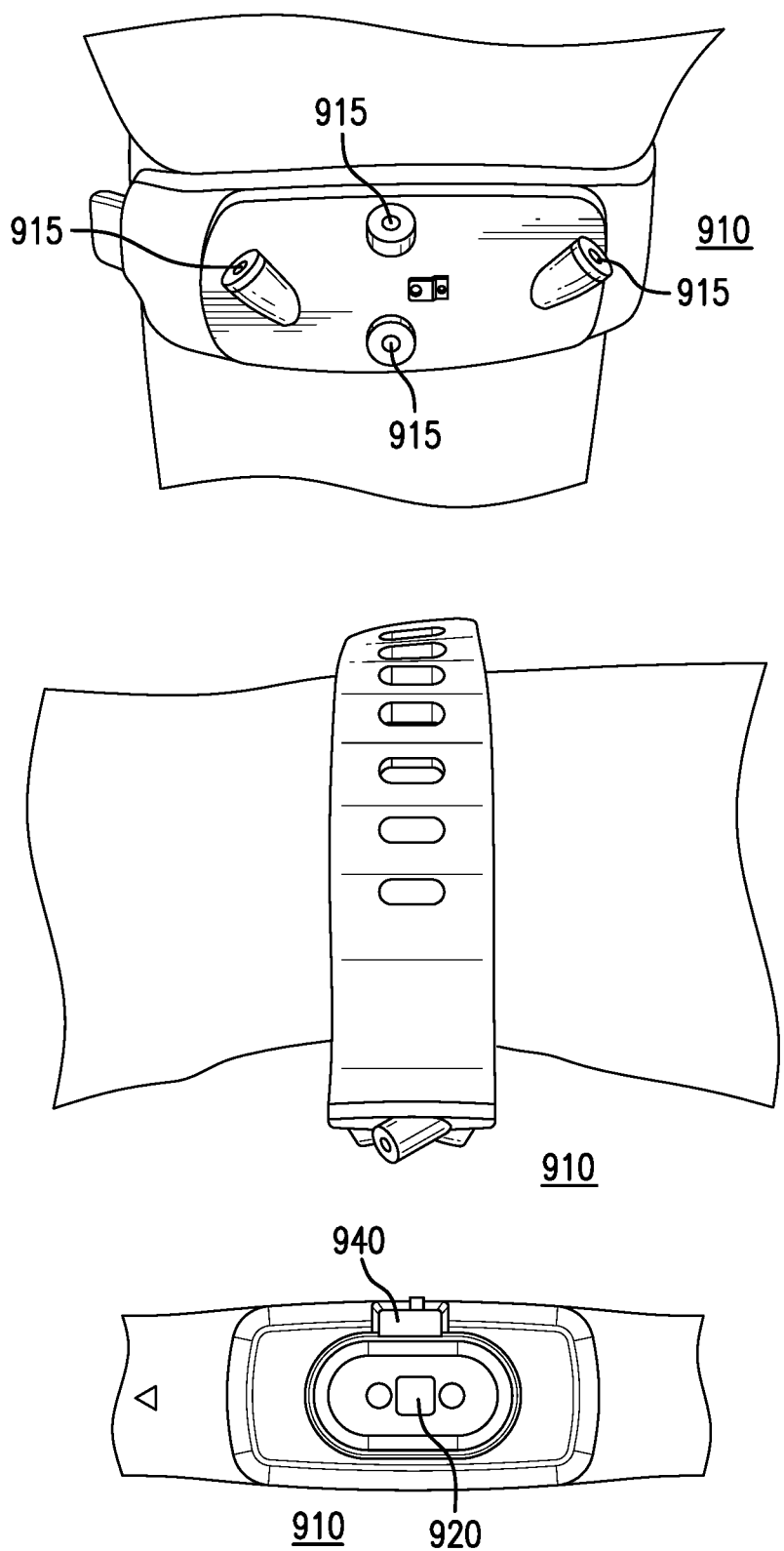
FIG. 9 depicts orthogonal views of an exemplary embodiment of the present inventive device.

FIGS. 7-10 depict views of exemplary sensor devices according to the present invention. FIG. 7A shows a top view of sensor device (710), FIG. 7B shows a side view of sensor device (710), and FIG. 7C shows the bottom view of sensor device (710). Thermal sensors (715) are shown arrayed around sensor device (710). None of thermal sensors (715) is oriented to face the same direction. However, no disclosure herein should be understood to mean that sensor device (710) or any other device according to the present invention cannot include two or more thermal sensors that are oriented to face the same direction. Device (710) may include a photoplesmography (PPG) heart rate sensor (720) and battery charging pads (730). FIG. 8 depicts orthogonal views of an enclosure for device (710) with apertures (725) for thermal sensors (715).

FIGS. 9A-9C depict views of device (910) having four thermopile sensors (915), arranged on the top surface of device (910). None of the thermopiles (915) are oriented in a direction parallel to any of the other thermopiles (915). Device (910) may also include an optional optical sensor, such as an APDS-9960. The bottom view shows an optional PPG heart rate sensor (920) and an optional power switch (940).

Figure 10:
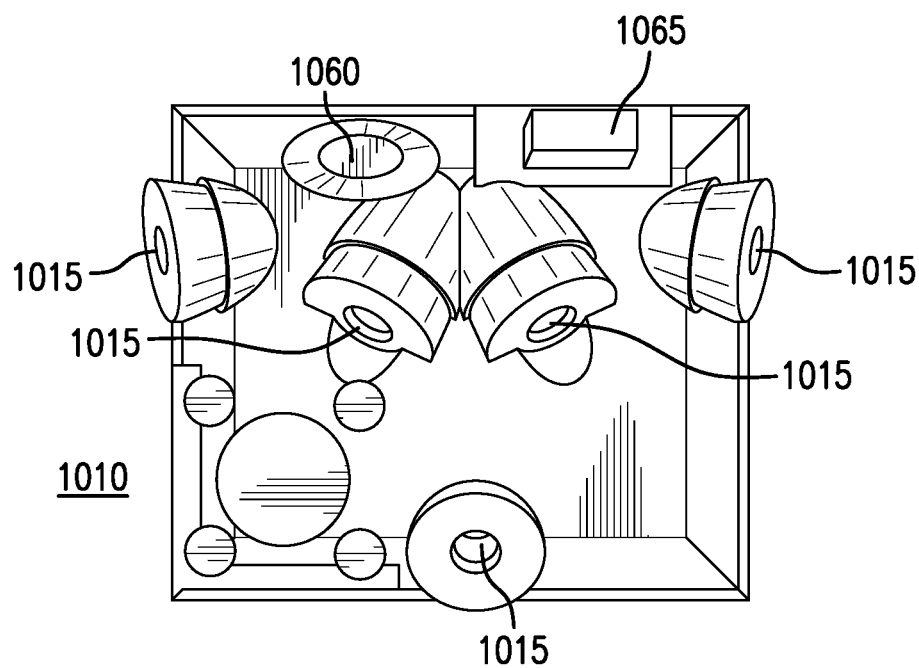
FIG. 10 depicts orthogonal views of an enclosure for a device having five thermopile sensors.
Figure 10:
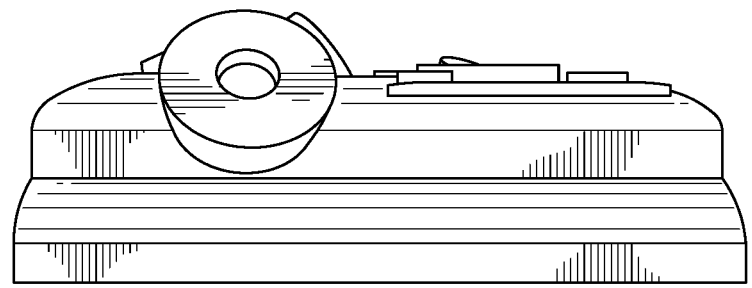
Figure 10:
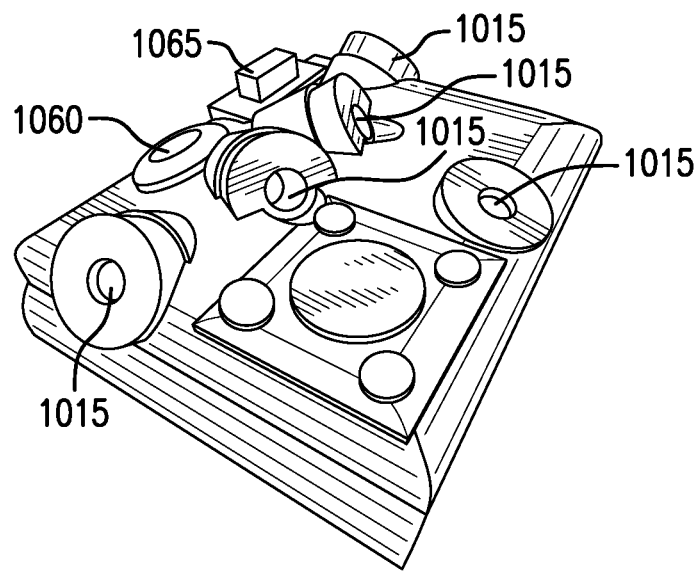

FIG. 10 depicts enclosure (1010) for an alternative embodiment having five thermopile sensors (1015), arranged on the top surface. In additional to the thermopile sensors, the sensor device having enclosure (1010) may include a button (1060) to allow the user to interact with the device, such as by deactivating a vibration motor. The sensor device may also include switch (1065) that, for example, allows the user to turn the device on and/or off. The sensor device may further include an indicator LED to provide visual feedback to the user, including an indication that data is being transmitted to the device and/or data is being transmitted from the device.

Figure 11:
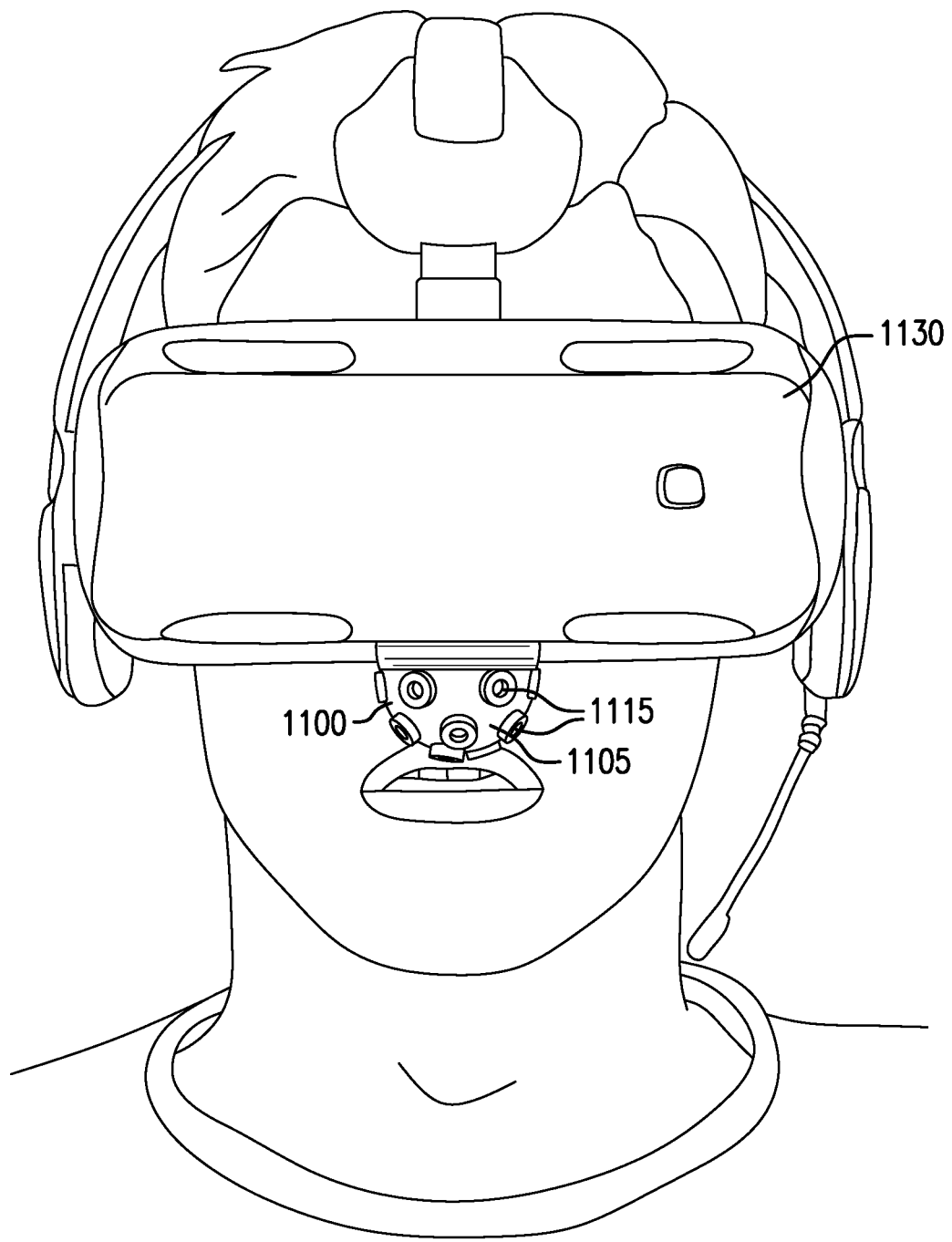
FIG. 11 depicts an exemplary embodiment of the present inventive device as applied to a head tracking unit.

FIG. 11 depicts sensor device (1100) with thermal sensor array (1105) having thermal sensors (1115). Sensor device (1100) is shown as mounted on virtual reality (VR) or augmented reality (AR) headset (1130). Using multiple thermal sensors (1115) with or without one or more inertial measurement units (IMU) such as an accelerometer allows sensor device (1100) to collect data that can be used to differentiate between distinct head movements and head positions which overlap in angular position. For example, head tracking based purely on an IMU sensor might not generate sufficient data to differentiate between a user nodding their head and a user leaning their torso forward. By using thermal sensor array (1105), it is possible to differentiate between a bow and a nod, greatly increasing the realism and immersiveness of some VR and AR experiences. The same thermal sensor array could also be placed on the underside of a drone to help it avoid colliding with people. The thermopile array may also be used to make robotic applications safer by, for example, placing the array on a dangerous or fragile robotic arm to monitor proximity to human bodies.

Figure 12:
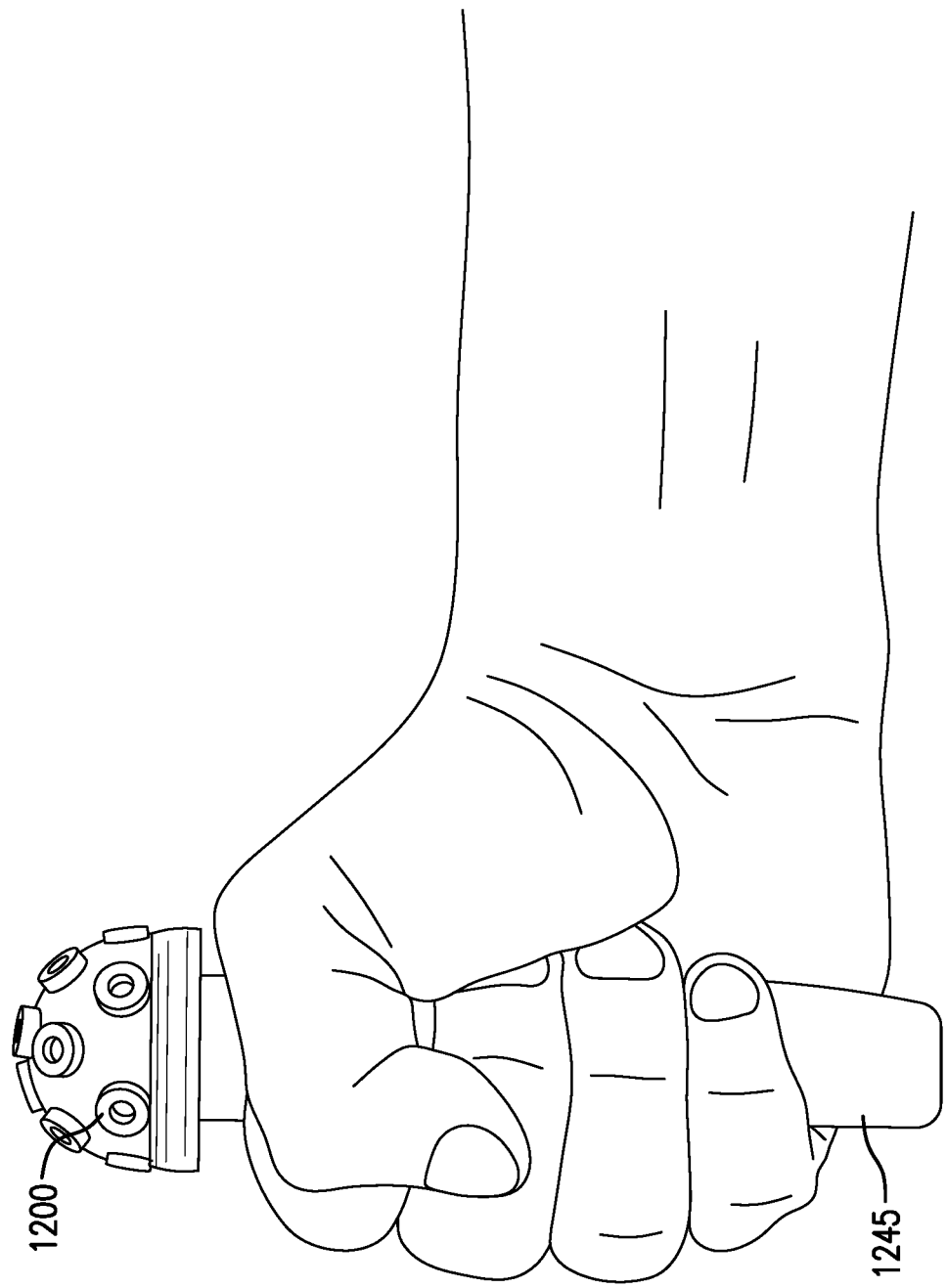
FIG. 12 depicts an exemplary embodiment of the present inventive device as applied to a hand-held controller.

As shown in FIG. 12, thermopile array (1200) in accordance with the present invention may be placed on a hand-held controller (1245) used for gaming, VR, AR, or control of remote devices such as aerial drones. Controller (1245) may also include one or more triggers, function buttons, joysticks, directional pads, thumb pads or other controls (not shown) depending on the application for which it is used.

Figure 13:
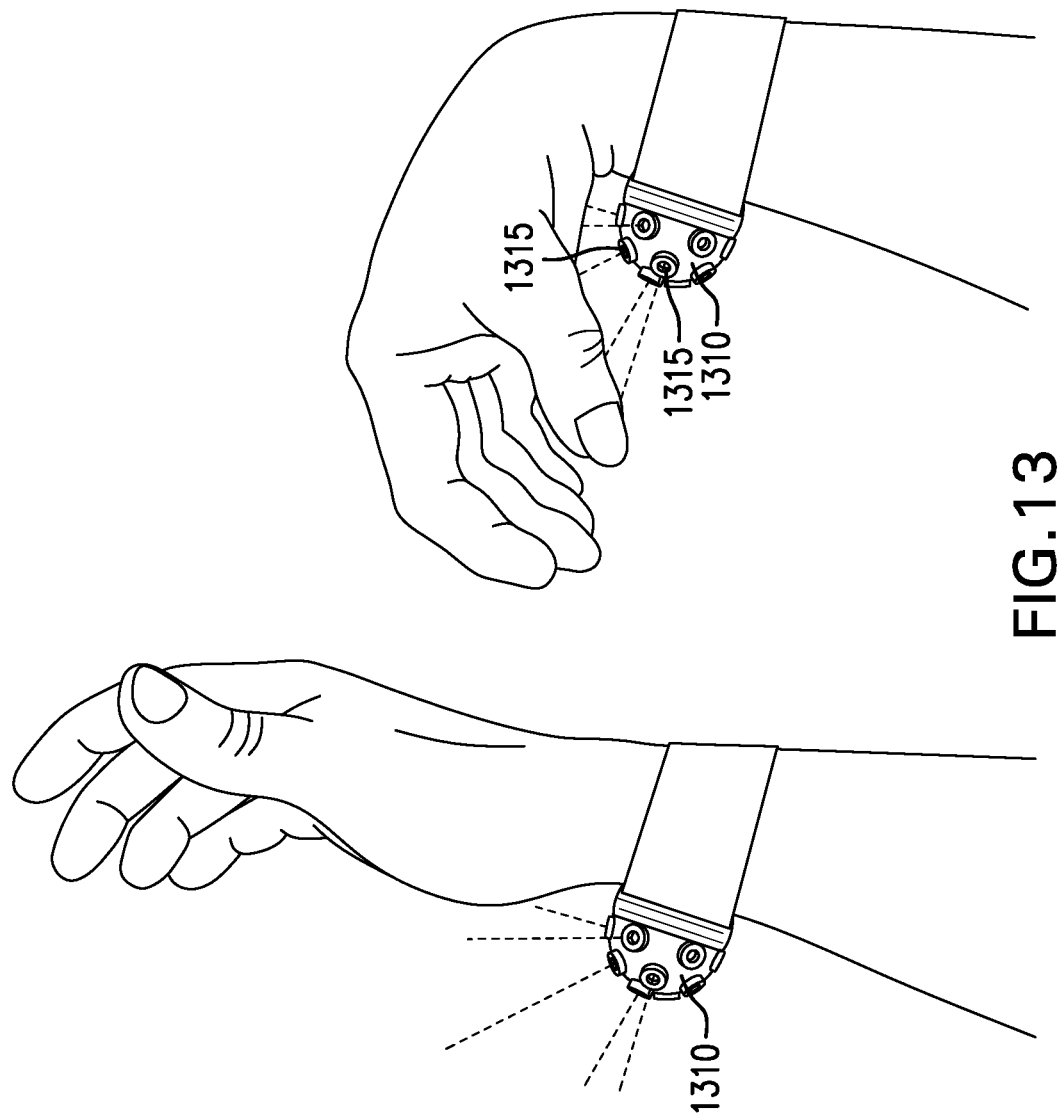
FIG. 13 depicts an exemplary embodiment of the present inventive device as applied to a strap worn around a user's wrist.

A thermopile array in accordance with the present invention may also be used to sense the position of parts of the body, such as a hand or fingers, relative to the user's body in 3D coordinate space. For example, as illustrated in FIG. 13, sensor device (1310) in accordance with the present invention may be used to recognize finger and/or hand gestures, including gestures that comprise American Sign Language. Preferably, to recognize finger and/or hand gestures, one or more thermopile sensors (1315) may be oriented to face the user's fingers and/or hand.

Figure 14:
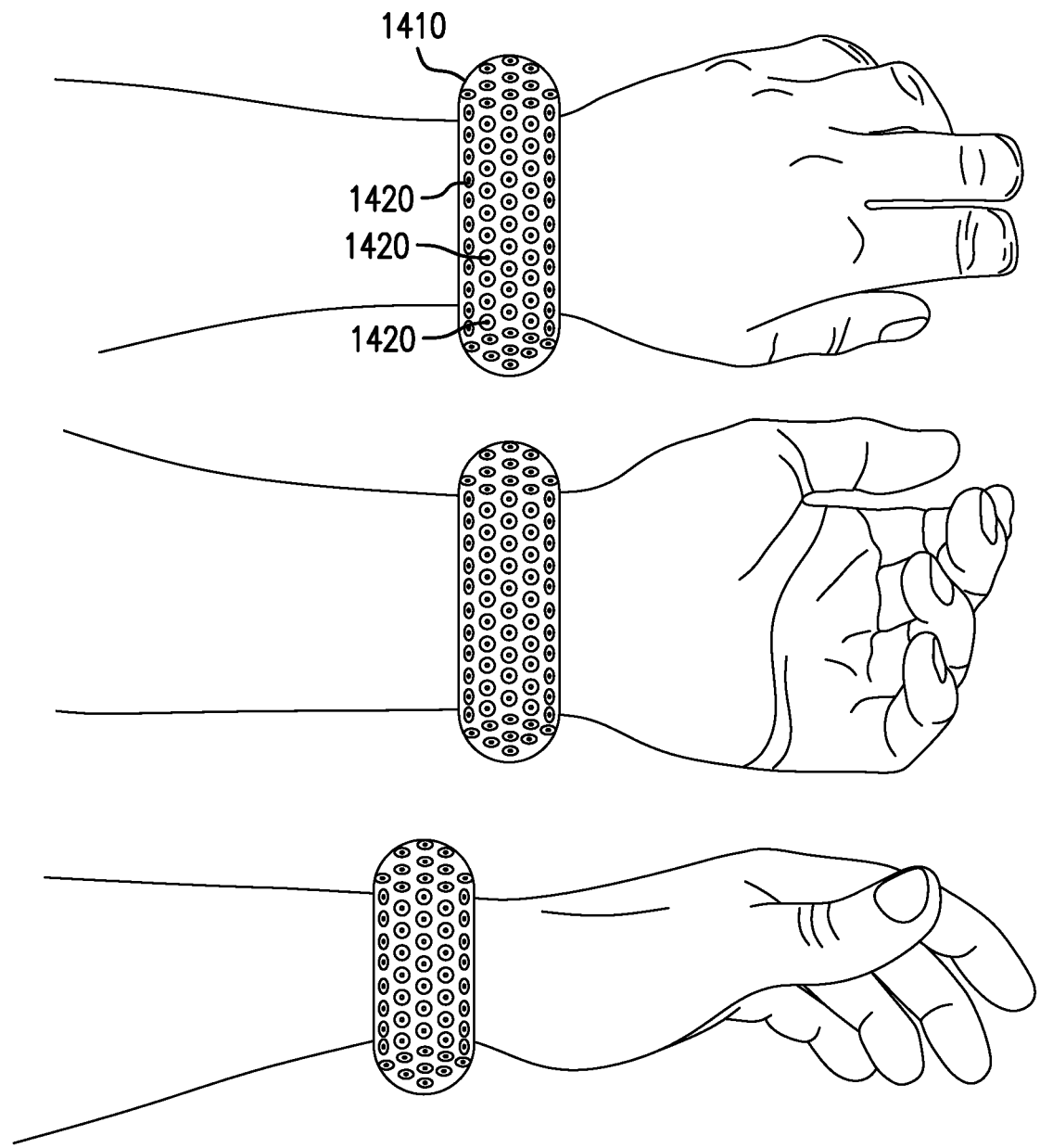
FIG. 14 depicts an exemplary embodiment of the present inventive device.

One way to determine position of the hand relative to the body is with a full 6 degrees of freedom (6DOF). The angular position of the hand (where it's pointing) and coordinate position of the hand may be determined simultaneously. Sensor device (1410) illustrated in FIG. 14 is a toroidal array of thermopiles (1420). The array may or may not include sensors that point toward the wrist. Sensor device (1410) would allow array coverage of the torso at all times, and may allow capturing the position of the hand relative to the torso in 6DOF.

Figure 15:
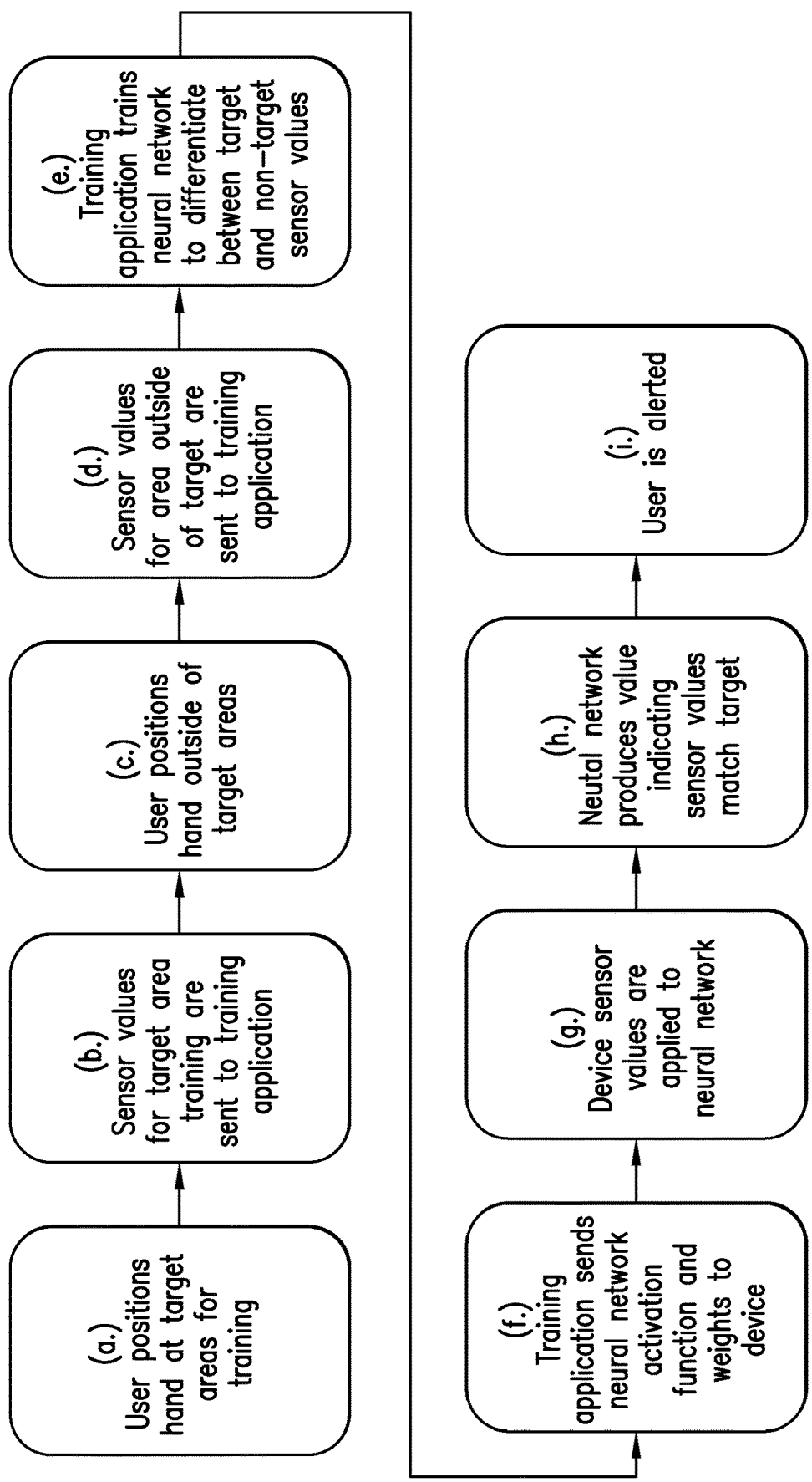
FIG. 15 depicts a flowchart of behavior modification training using an exemplary embodiment of the present inventive device.
Figure 16:
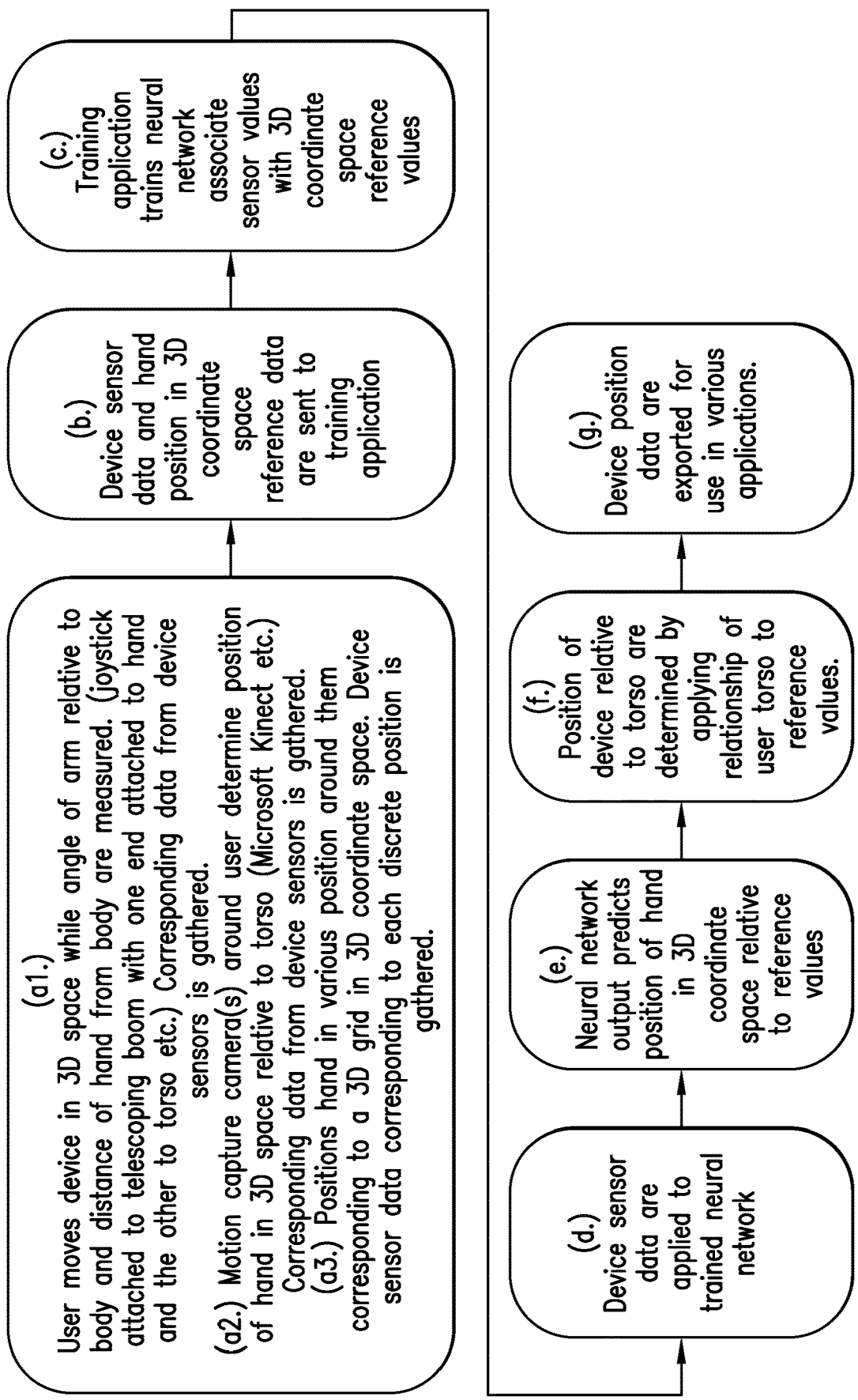
FIG. 16 depicts a flowchart of position training to output data using an exemplary embodiment of the present inventive device.

FIGS. 15 and 16 are flowcharts showing methods of practicing embodiments of the present invention. FIG. 15 is a flowchart reciting use of a device for, for example, behavior modification. Steps (a) and (b) recite positioning the hand (e.g., with a device attached to the user's hand, arm, or wrist) and collecting sensor data corresponding to a target area. That data may be saved to memory and/or sent to a training application. Steps (c) and (d) recite re-positioning the hand (and therefore the device) and collecting sensor data corresponding to one or more areas outside the target area. That data may be saved to memory and/or sent to a training application.

Figure 15A:
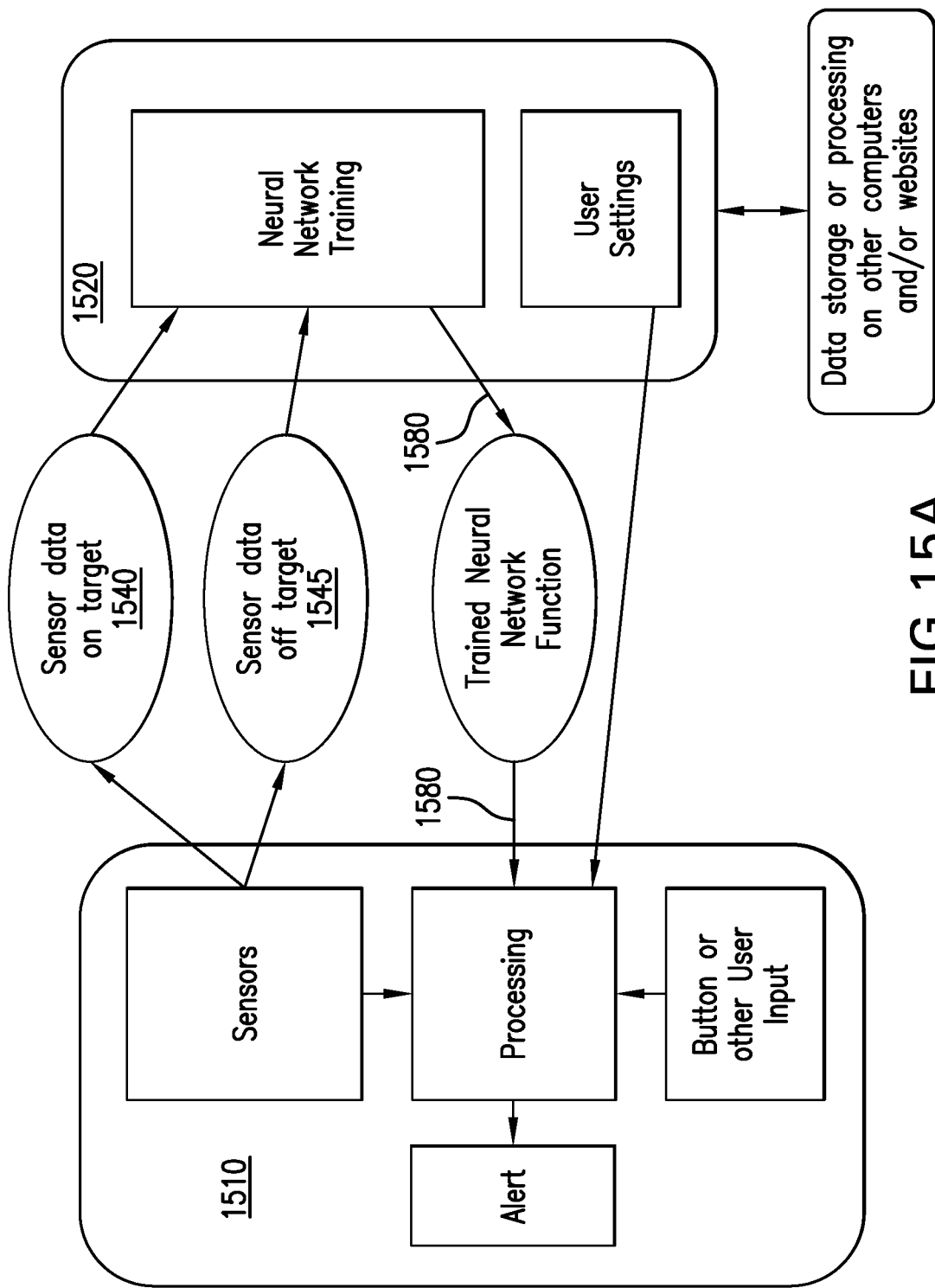
FIG. 15A depicts a flowchart reflecting transfer of data, settings and a trained neural network function between a sensor device and a separate device.

The training application may be stored on the device or may be on a separate device. FIG. 15A depicts sensor device (1510) and separate device (1520). In the exemplary embodiment depicted in FIG. 15A, the neural network training application is located on separate device (1520). "Target" or "on-target" sensor data (1540), i.e., data collected when sensor device (1510) is oriented toward a user's head, and "off-target" or "non-target" sensor data, i.e., data collected when sensor device (1510) is oriented away from a user's head, may be transfer from sensor device (1510) to the network training application in separate device (1520). In the alternative, the neural network training application may be located on sensor device (1510).

Figure 15B:
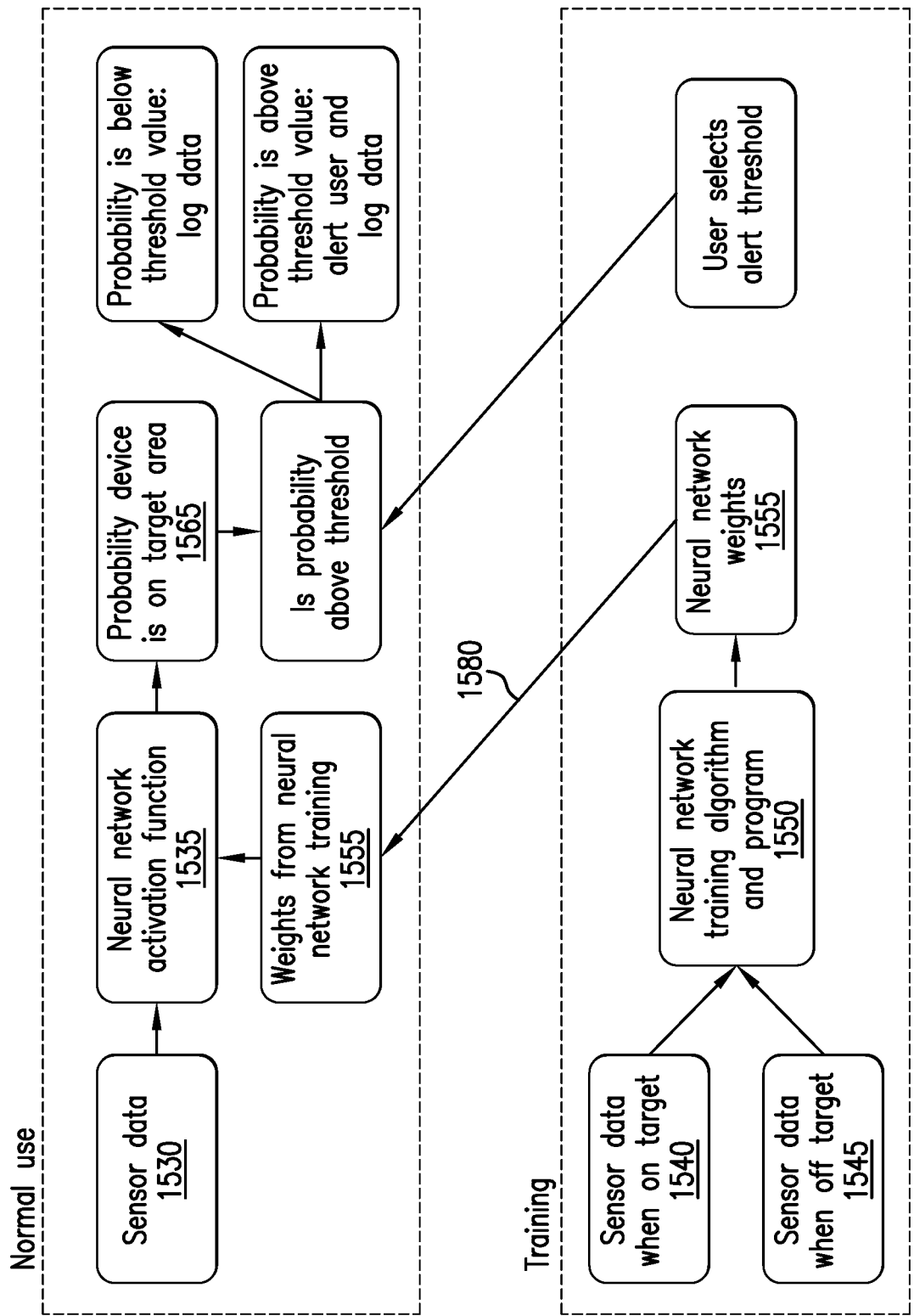
FIG. 15B depicts a flowchart reflecting the process for training and applying a neural network algorithm.

At Step (e), the training application trains a neural network to differentiate between target and non-target sensor values. Referring to FIG. 15B, "on-target" data (1540) and "off-target" data (1545) form a combined data set that is processed by a neural network algorithm and program (1550). The neural network algorithm and program generates neural network weights (1555) using common machine learning techniques, such as those discussed in the publication, Derek D. Monner & James A. Reggia, *A generalized LSTM-like training algorithm for second-order recurrent neural networks*, Neural Networks, January 2012, at 70.

At Step (f), if the training application is located on a separate device, the separate device may send a neural network activation function and weights to the device, shown by arrows (1580) in FIGS. 15A and 15B. In the alternative, the training application may be stored on the device and the neural network activation function and weights may be transferred to memory in the device.

At Step (g) in FIG. 15, and as depicted as "Normal Use" in FIG. 15B, the device is used for the intended function, such as behavior modification. The sensors on the device generate sensor data values (1530) and those values are processed by neural network activation function (1535) using the weights (1555) from the neural network training. At Step (h), the neural network generates a value response indicating whether the sensor values match the target. The value response generated by the neural network may be a percentage reflecting the probability (1565) that the sensor values match the target. In Step (h) of FIG. 15, the value response may be high enough to indicate that the values match the target, and at Step (i) the user may be alerted that unwanted behavior is occurring. A predetermined threshold value may be selected by the user, and may be used to determine whether the value response indicates that the values match the target.

FIG. 16 is a flowchart reciting three alternative methods of device training and position triangulation. In each alternative, the 3D position of the hand is measured, in addition to collecting sensor data corresponding to a target area and one or more non-target areas as described in Steps (a)-(d) for FIG. 15 above. At Step (a1), the user may move the device in 3D space while the angle of the user's arm relative to the user's body and the distance of the user's hand from the user's body are measured. Alternatively or in addition, at Step (a2), one or more motion capture cameras may be used to determine the position of a user's hand in 3D space relative to the user's torso. Alternatively or in addition, at Step (a3), the user's hand may be positioned in various positions around the user corresponding to a 3D grid in 3D coordinate space. For each alternative, data from sensors corresponding to the positions of the device is gathered. At Step (b) device sensor data and hand position in 3D coordinate space reference data are sent to a training application. As described above for the method shown in FIG. 15, the training application may be stored on the device held or worn by the user, or may be stored on a separate device. If the training application is stored on a separate device, the separate device may send a neural network activation function and weights to the device held or worn by the user.

At Step (c) of FIG. 16, a training application trains a neural network, associating sensor values with 3D coordinate space reference values. At Step (d), device sensor data is applied to the neural network. The neural network output may be used to predict the position of the user's hand in 3D coordinate space relative to reference values (Step (e)) and the position of the device relative to the user's torso may be determined by applying a relationship of the user's torso to reference values (Step (f)). At Step (g), the device position data may be exported to another device to be used in various applications, including a video game console, a virtual reality or augmented reality device, or a surgical simulator.

Figures 17A, 17B:
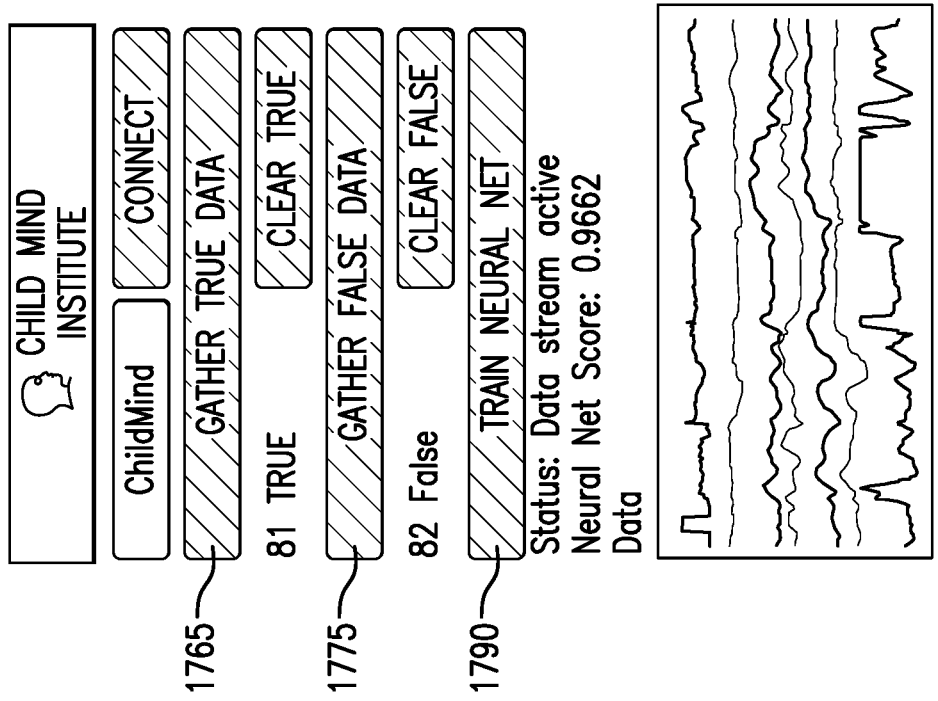
FIG. 17A depicts an exemplary neural network architecture for a training application using an exemplary embodiment of the present inventive device.
FIG. 17B depicts a screenshot from a sample behavior modification device training and management application according to the present invention.
Figure 18:
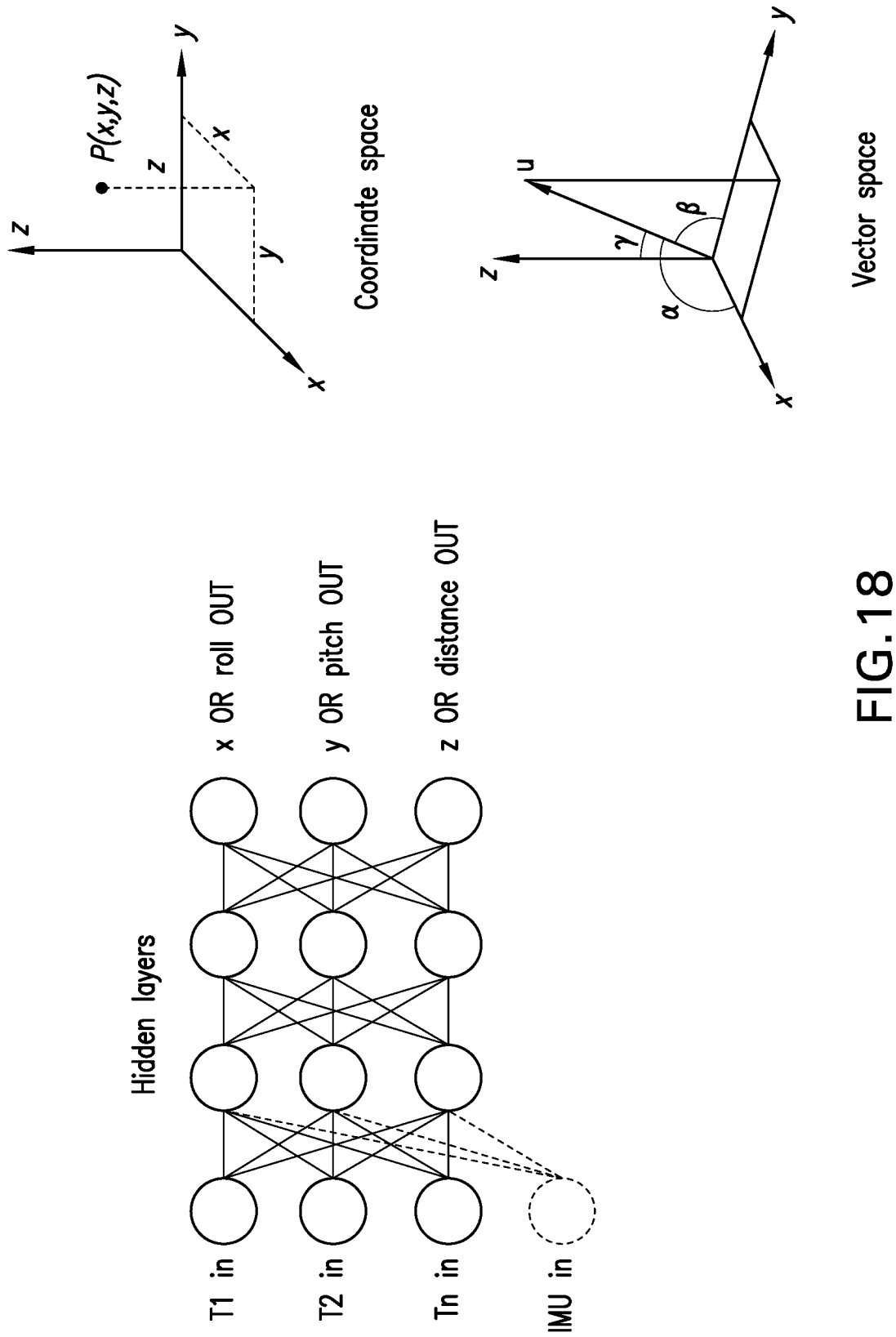
FIG. 18 depicts an exemplary neural network architecture for a training application using an exemplary embodiment of the present inventive device.
Figure 19:
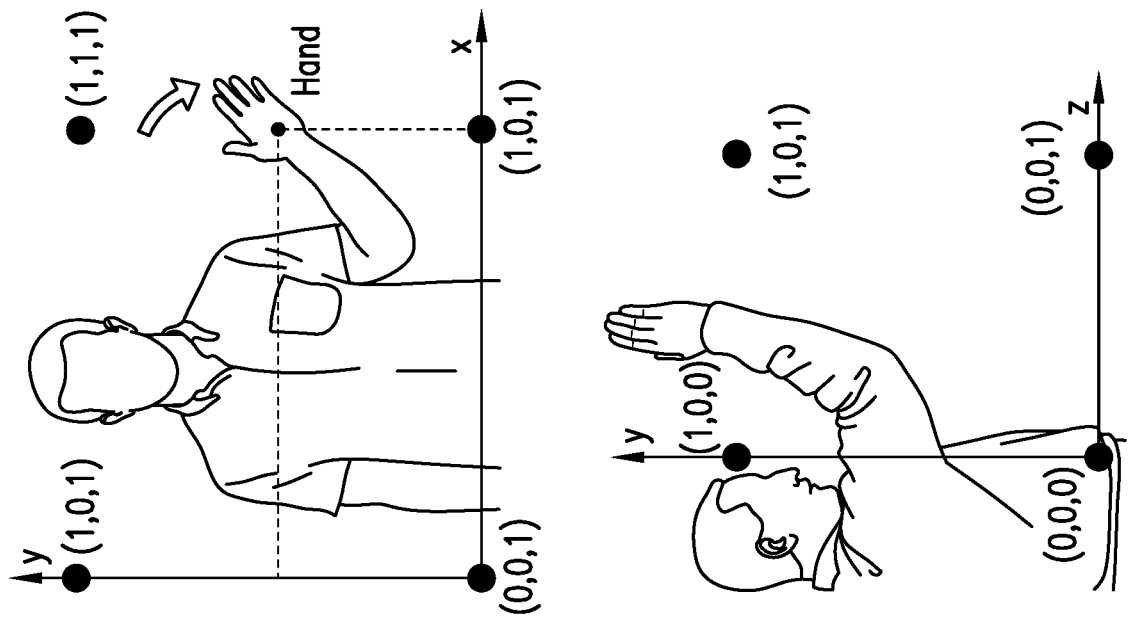
FIG. 19 depicts an exemplary neural network architecture for a training application using an exemplary embodiment of the present inventive device.
Figure 19:
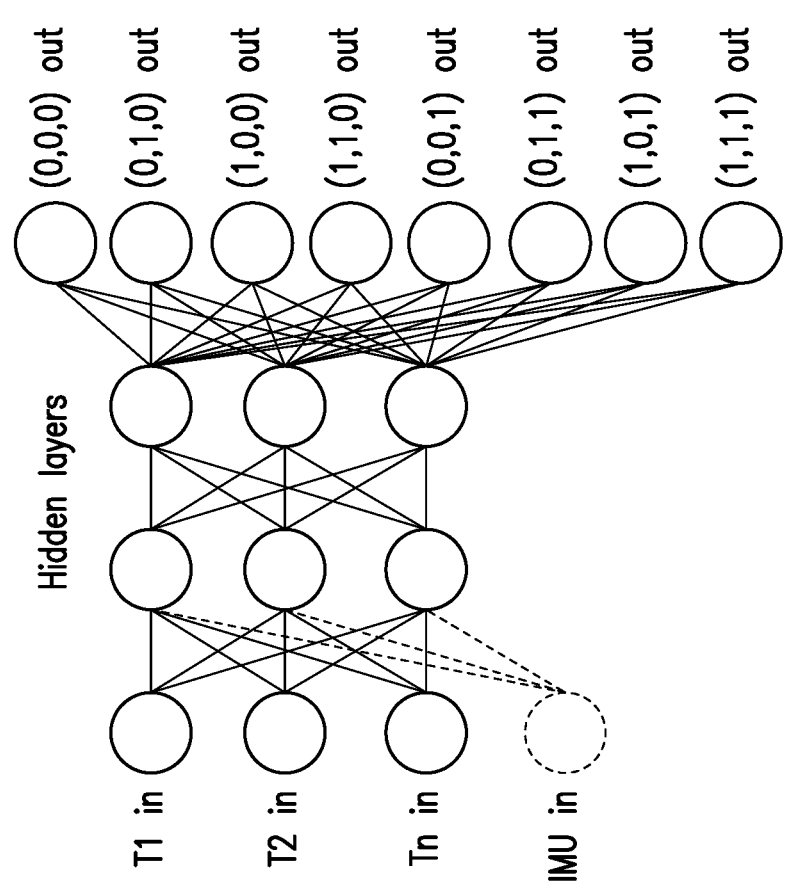

FIGS. 17-19 are visual depictions of training applications and neural networks. FIG. 17A is visual depiction of a multi-layer perceptron (MLP) long short-term memory (LSTM) neural network architecture used to process raw sensor data and determine the probability that the device is positioned toward the target. There is a single output (1720): probability that the device is positioned toward the target. Thermopile sensor array input nodes (T1 in, T2 in . . . Tn in) are shown for thermopile sensor array inputs. The number of thermopile sensor array inputs may be one or two, but preferably the number of thermopile sensor array inputs is three or more.

Also, IMU sensor input node (1730), shown by dotted lines, is optional. If included, the IMU sensor may determine very broad information about proximity of the device to the target, for example whether the user has raised their hand above their shoulders. The IMU may also be used to determine when to run the neural network activation function or sample the thermopile sensors by, for example, detecting when the device is close enough to the target to warrant such computational resources. For example, if the target is the area above the ear and the user's hand is next to their waist, no thermopile sensor data may be gathered and no neural network calculations may be made. When the IMU sensor data are compared to the average target IMU sensor reading and the two are similar enough, for example if the previously mentioned user raised their hand with the device above their chest, thermopile sensor sampling and neural network activation function calculation may begin for fine-grain detection of the target area.

FIG. 17B depicts a screenshot from a sample behavior modification device training and management application. The application may be run from a separate device such as a smart phone or a laptop computer. The graph at the bottom of the screen shows sample live sensor data. The user may first connect the sensor device to the separate device, either by a wired or wireless connection. The time set on the sensor device may then be matched to the time on the separate device to assure continuous data streaming and to initiate graphical depiction of device sensor data in the mobile app.

The user may place his/her hand at the target location and initiate data collection by, for example, selecting a "gather true data" button (1765) on the screen of the separate device. The application may then gather data about the target until the user stops data collection by, for example, selecting a "stop" button (not shown) on the screen of the separate device. While data is being gathered, the user may move his/her hand around the target and in various positions and angles around the target to ensure full coverage. The user can move his/her hand over a large area to create a large target, or keep the device hovering around a single point to make target detection as specific as possible. The user may stop data collection, move his/her hand to another area, restart data collection and then stop it again to target two entirely different areas which may be highly distinct. The user can collect data in that way for any number of areas.

The user may then move his/her hand to a position that is not at a target area and initiate data collection again by, for example, selecting a "gather false data" button (1775) on the screen of the separate device. The user may move his/her hand over a variety of areas which are not targeted, preferably including boundary areas. For example, to target an area above one or both of the user's ears, because the target areas and the user's face would be fairly similar in terms of sensor values, the user could pan the device across the user's face while gathering false data to find a contrast between the target and non-target areas. The user could also wave his/her hand around them to pick up random background data to augment differentiation of the target from whatever is found in the surrounding environment.

When both "true" on-target data and "false" off-target data have been gathered, the user may initiate creation of a trained neural network activation function and accompanying neural network weights by, for example, selecting a "train neural network" button (1790) on the screen of the separate device. The activation function is standard to the neural network architecture and may be stored on the sensor device firmware or a separate device. If the activation function is stored on a separate device, once the training is complete, an application on the separate device may send the neural network weights to the sensor device. The sensor device is able to apply its sensor data combined with trained neural network weights to the neural network activations function "equation" to arrive at a probabilistic estimate of whether the sensor device is near the target.

FIG. 18 depicts a neural network architecture and simple 3D coordinate position triangulation context for a position determination device. At least three thermopile sensor input nodes are shown. That number may be higher or lower. Preferably at least six thermopile sensor input nodes are included. IMU sensor input node and connections, shown with dotted lines, are optional.

The position determination the sensor device may be used to assess—position in 3D coordinate space—has three values: x,y and z coordinate values (or roll and pitch euler angles (direction) plus distance for vector format). A minimum of three output nodes for the data processing neural network would be used. To train the absolute position device, reference data may be used. Sources of reference data might include, for example, 3D position cameras like Leap Motion™ and Microsoft Kinect™, computer modeling using a thermal body of a human body and surrounding environment, or a joystick and distance sensor held by the hand and connected to the torso by a boom.

FIG. 19 depicts a neural network architecture and heat map-based 3D coordinate position triangulation context for an absolute position determination device. Sensor data may be gathered at specific positions, and the probability that the device is at one of those positions may be calculated. The probabilities that the device is at each of the trained positions may be combined into a probability gradient between all the positions to form a heat map. Each position in the heat map grid may be an output node in the neural network. The addition of more heat map positions increases the resolution of the heat map and the accuracy of the positions in 3D coordinate space thus triangulated. The heat map allows more control over what contextual information is prioritized.

While the invention has been described with reference to the preferred embodiment and alternative embodiments, which embodiments have been set forth in considerable detail for the purposes of making a complete disclosure of the invention, such embodiments are merely exemplary and are not intended to be limiting or represent an exhaustive enumeration of all aspects of the invention. Further, it will be apparent to those of skill in the art that numerous changes may be made in such details without departing from the spirit and the principles of the invention. It should be appreciated that the invention is capable of being embodied in other forms without departing from its essential characteristics.

What is claimed is:

1. A device for determining position comprising:
a thermal sensor configured to output temperature data related to a temperature of an object in a field of view of the thermal sensor;
a proximity sensor;
a relative position sensor;
a memory containing machine-readable medium comprising machine executable code; and
one or more processors coupled to the memory, said one or more processors configured to execute the machine executable code, wherein the machine executable code causes the one or more processors to:
receive a set of sensor data comprising data output from the thermal sensor, the proximity sensor, and the relative position sensor;
process the set of sensor data using a machine learning algorithm to determine a position of the device relative to a user of the device; and
export to a receiving device data corresponding to the position of the device as determined by the machine learning algorithm;
wherein the position of the device is a three-dimensional position in space.

2. The device of claim 1, wherein the set of sensor data comprises multiple sensor readings from each of the thermal sensor, the proximity sensor, and the relative position sensor.

3. The device of claim 2, wherein the machine learning algorithm comprises a neural network.

4. The device of claim 1, wherein the thermal sensor comprises three thermopiles.

5. The device of claim 4, wherein each thermopile is oriented in a direction that is not parallel to the orientation of any of the other thermopiles.

6. The device of claim 1, wherein the proximity sensor is an infrared sensor.

7. The device of claim 6, wherein the infrared sensor is capable of emitting and receiving infrared radiation.

8. The device of claim 1, wherein the receiving device is a video game console.

9. The device of claim 1, wherein the receiving device is a surgery simulator.

10. The device of claim 1, wherein the relative position sensor is an accelerometer, a gyroscope, or a magnetometer.

11. A system for determining position comprising:
a device comprising a thermal sensor configured to output temperature data related to a temperature of an object in a field of view of the thermal sensor, a proximity sensor, and an accelerometer;
a motion capture camera;
a memory containing machine readable medium comprising machine executable code; and
one or more processors coupled to the memory;
wherein the one or more processors are configured to execute the machine executable code to:
receive a set of sensor data comprising data output from the thermal sensor, the proximity sensor, the accelerometer, and the motion capture camera;
process the set of sensor data using a machine learning algorithm to determine an angular and a three-dimensional position of the device; and
export to a receiving device data corresponding to the position of the device as determined by the machine learning algorithm.

12. The system of claim 11, wherein the memory and one or more processors are located within the device.

13. The system of claim 12, wherein the proximity sensor is an infrared sensor.

14. The system of claim 11, wherein the set of sensor data comprises multiple sensor readings from each of the thermal sensor, the proximity sensor, and the accelerometer.

15. The system of claim 14, wherein the machine learning algorithm comprises a neural network.

16. The system of claim 11, wherein the thermal sensor comprises three thermopiles.

17. The system of claim 16, wherein each thermopile is oriented in a direction that is not parallel to the orientation of any of the other thermopiles.

18. The system of claim 11, wherein the one or more processors are configured to output on a display screen an indication corresponding to the angular and three-dimensional position of the device.

19. The system of claim 11, wherein the receiving device is a video game console.

20. The system of claim 11, wherein the receiving device is a surgery simulator.

* * * * *